US012648799B2

(12) United States Patent
Simpson et al.

(10) Patent No.: US 12,648,799 B2
(45) Date of Patent: Jun. 9, 2026

(54) DEVICES, SYSTEMS AND METHODS FOR SI JOINT TREATMENT

(71) Applicant: LEGACY SURGICAL LLC, Austin, TX (US)

(72) Inventors: Josh Simpson, Austin, TX (US); Lee Strnad, Richfield, OH (US); Dave Lamb, Round Rock, TX (US)

(73) Assignee: Legacy Surgical, LLC, Austin, TX (US)

( * ) Notice: Subject to any disclaimer, the term of this patent is extended or adjusted under 35 U.S.C. 154(b) by 0 days.

(21) Appl. No.: 19/336,996

(22) Filed: Sep. 23, 2025

(65) Prior Publication Data

US 2026/0083483 A1 Mar. 26, 2026

Related U.S. Application Data

(60) Provisional application No. 63/698,011, filed on Sep. 23, 2024.

(51) Int. Cl.
*A61B 17/70* (2006.01)
*A61B 17/86* (2006.01)

(52) U.S. Cl.
CPC ........ *A61B 17/7055* (2013.01); *A61B 17/702* (2013.01); *A61B 17/862* (2013.01); *A61B 17/863* (2013.01)

(58) Field of Classification Search
CPC . A61B 17/702; A61B 17/7055; A61B 17/862; A61B 17/863
See application file for complete search history.

(56) References Cited

U.S. PATENT DOCUMENTS

| | | | | |
|---|---|---|---|---|
| 5,443,467 A * | 8/1995 | Biedermann | ...... | A61B 17/7037 |
| | | | | 606/328 |
| 5,628,740 A * | 5/1997 | Mullane | ............ | A61B 17/7041 |
| | | | | 606/307 |
| 2006/0025771 A1* | 2/2006 | Jackson | ............ | A61B 17/7032 |
| | | | | 606/273 |
| 2006/0095038 A1* | 5/2006 | Jackson | ............ | A61B 17/7037 |
| | | | | 606/306 |
| 2007/0014649 A1* | 1/2007 | James | ............... | A61B 17/8685 |
| | | | | 411/81 |
| 2007/0282342 A1* | 12/2007 | Niederberger | ....... | A61B 17/863 |
| | | | | 606/249 |
| 2013/0018427 A1* | 1/2013 | Pham | ................. | A61B 17/8695 |
| | | | | 606/301 |
| 2014/0031934 A1* | 1/2014 | Trieu | ................. | A61B 17/8685 |
| | | | | 623/17.11 |

(Continued)

*Primary Examiner* — Nicholas J Plionis
(74) *Attorney, Agent, or Firm* — BRAINSPARK ASSOCIATES, LLC

(57) ABSTRACT

Disclosed are devices, systems and methods for inserts for sacroiliac joint arthroplasty, which can include the employment of a longitudinal bone screw and associated threaded cylindrical sleeve, received on a proximal end of the bone screw, with a collet, nut or other securement feature holding the sleeve onto the screw. The sleeve can selectively articulate and/or be immobilized relative to the bone screw, with the system allowing for, at a surgeon's option, motion preservation between bone surfaces in some surgical applications while being utilized as an immobilizing and/or fusion construct between bone surfaces during other surgical applications.

20 Claims, 21 Drawing Sheets

100

110

120

130

(56)          References Cited

U.S. PATENT DOCUMENTS

| | | | |
|---|---|---|---|
| 2014/0277139 A1* | 9/2014 | Vrionis | ................. A61B 17/70 |
| | | | 606/246 |
| 2017/0296245 A1* | 10/2017 | Gault | .................... A61B 17/68 |
| 2018/0228621 A1* | 8/2018 | Reiley | ................. A61B 17/866 |
| 2023/0285156 A1* | 9/2023 | Sansur | ............... A61F 2/30988 |

* cited by examiner

600

680

700

710

ß

Posterior Iliac
Spine of the Left
Ilium

Vertebra
L4

Vertebra
L5

Left
Ilium

Sacrum
S1

Sacroiliac
Joint (SI-Joint)

Sacrum

Femur

Femur

Vertebra
L4

Vertebra
L5

Left
Ilium

Posterior Iliac
Spine of the Left
Ilium

Sacral
Alae

Sacroiliac Joint
(SI-Joint)

Sacrum

DEVICES, SYSTEMS AND METHODS FOR SI JOINT TREATMENT

CROSS-REFERENCE TO RELATED APPLICATIONS

This application claims the benefit of U.S. Provisional Application No. 63/698,011 entitled "DEVICES, SYSTEMS AND METHODS FOR SI JOINT TREATMENT" filed Sep. 23, 2024, the disclosure of which is incorporated by reference herein in its entirety.

FIELD OF THE INVENTION

The present subject matter relates generally to implants and related devices used in surgeries of the human body, including orthopedic implants such as joint and/or bone implants used in in sacral-iliac surgeries and/or other orthopedic procedures. More specifically, the disclosed implants can desirably be implanted to selectively either preserve a range of motion of the SI joint so that the joint's synergistic shock absorbing mechanism remains intact and/or functional while maintaining joint stabilization and/or be utilized to reduce mobility, immobilize and/or fuse motion of the SI joint.

BACKGROUND OF THE INVENTION

The human hip girdle is made up of three large bones joined by three joints. One of the bones is called the sacrum and it lies at the bottom of the lumbar spine, where it connects with the L5 vertebra. The other two bones are commonly called "hip bones" and are technically referred to as the right ilium and the left ilium. The sacrum connects with both hip bones at the sacroiliac joint (in shorthand, the SI-Joint). The sacro-iliac joint is a diarthrodial joint that joins and links the iliac bones (pelvis) to the sacrum (lowest part of the spine above the tailbone) and is an essential component for shock absorption to prevent impact forces from reaching the spine and hip joint. The SI joint is the articulation of the sacrum and an iliac crest. It allows the pubic symphysis to open, close and rotate about the joint bilateral SI joints. The SI joint includes chondro-cartilage, fibrocartilage and nociceptive nerves, with the hyaline cartilage of the sacral surface moving against fibrocartilage of the iliac surface.

The SI-Joint functions in the transmission of forces from the spine to the lower extremities, and vice-versa. The SI-Joint has been described as a pain generator for up to 22% of lower back pain. Like any other joint in the body, the SI joint can be injured and/or become degenerative. Pathological conditions which can affect a sacroiliac joint include degenerative and inflammatory arthritis, posttraumatic and postpartum instability, infection and neoplastic disease, among many others. Various other conditions which might cause sacroiliac joint pain include leg-length discrepancy, hip arthritis, and lumbosacral fusions for low back pain, as well as iatrogenic violation of the joint following autologous posterior iliac crest bone graft harvest. When SI joint injury/degeneration occurs, the nociceptive nerves (when pinched from joint dysfunction) can lead to multiple locations of pain. SI joint pain can easily be confused with lumbar spine pain due to their similar clinically observed pain presentation. People can often feel pain in their buttocks and sometimes in the low back and legs. This is especially true while lifting, running, walking or even sleeping on the involved side. According to scientific data, it is common for pain from the SI joint to feel like disc or low back pain.

Current exams and SI joint pain diagnostics vary from injections to a 5-test exam including FABER, Compression, Thigh Thrust, Distraction, and Gaenslen. If 3 tests are positive for pain, or a patient has improvement of pain after an injection, then they are clinically diagnosed with sacro-iliac dysfunction based on provider judgment. The SI joint moves in a number of axes experiencing multidimensional forces. This joint moves slightly with the pubic symphysis with each step or flexion and extension of the waist; acting like a shock absorber between the lumbar spine and the hip joint.

To relieve pain generated from the SI Joint, sacroiliac joint fusion is typically indicated as surgical treatment, e.g., for degenerative sacroiliitis, inflammatory sacroiliitis, iatrogenic instability of the sacroiliac joint, osteitis condensans ilii, or traumatic fracture dislocation of the pelvis. Currently, screw and screw with plates and/or fusion implants are used for sacro-iliac fusion. At the same time the cartilage has to be removed from the "synovial joint" portion of the SI joint especially with a posterior fusion. This requires a large incision to approach the damaged, subluxed, dislocated, fractured, or degenerative joint. Fusion of the SI joint sends the mechanical load to the hips and lumbar spine causing further deterioration. This fusion causes the hip and lumbar spine to receive the majority impact of each step. That load would normally be shared by the SI joint causing peripheral joint deterioration.

Various studies have shown the SI joint to move 1.2 to 2.8 degrees for men and women respectively (Kiapour et al., 2019). SI joint dysfunction or sacroiliitis refers to the improper motion of the SI joint causing pain to the lower back and pelvis presenting in a number of different distributions of a pain and loss of mobility. It is also documented that the SI joint contains nociceptive receptors or pain receptors (Szadek et al., 2008). Therefore, if the SI joint is not functioning as intended it can cause compression of the nerves and/or other tissues within the joint creating pain. It will also increase wear and tear on the lumbar spine and hip joints.

Fusion of the SI joint varies with each currently available device, but all procedures to date rely on the concept of fusing the SI joint. During these procedures, a device or interbody is placed surgically, compressing and damaging the nerves that traverse through the joint. Such devices also eliminate the range of motion of the joint, further diminishing the synergistic shock absorption of the hip, SIJ and lumber spine (Cohen, 2005). Lastly, fusion of the SI joint can be a contraindication for vaginal delivery in women due to the loss of range of motion of the SI joint limiting pelvic expansion. Accordingly, there is need for further improvement in surgical implants, and the present subject matter is such improvement.

BRIEF SUMMARY OF THE INVENTION

The following presents a simplified summary of the subject matter in order to provide a basic understanding of some aspects of the subject matter. This summary is not an extensive overview of the subject matter. It is intended to neither identify key or critical elements of the subject matter nor delineate the scope of the subject matter. Its sole purpose is to present some concepts of the subject matter in a simplified form as a prelude to the more detailed description that is presented later.

Various embodiments herein disclose an implant for treating a degenerated and/or damaged sacral-iliac joint of a patient. In various embodiments, the implant can include a plurality of component parts which stabilize the bones of the sacral-iliac joint (e.g., the sacrum and a respective ilium) while desirably allowing these bones to glide, rotate and/or otherwise move in a controlled fashion. Desirably, the implant (dubbed the "Pelvaxis System" by the Applicant) can preserve some range of motion of the SI joint so that the joint's synergistic shock absorbing mechanism remains intact while maintaining joint stabilization. The system also desirably stabilizes the articulating bones of the SI joint a desired distance away from each other, such that the nerves and/or other tissues within the joint are not compressed and/or otherwise compromised.

In various embodiments, the decompression of the nerves and/or stabilization of the joint provided by the implant can allow for significant pain and symptom improvement. If the pain levels are improved with the implant stabilization and the patient's cartilage regenerates, it is possible for the implant to be extracted at a future time once the injury heals. In some embodiments, only a single implant and/or a pair of implants may be required for a desired treatment, while in other embodiments additional implants (e.g., a third, fourth implant and so on) can be inserted, if necessary. Such additional implants may be implanted at the time of initial implantation and/or at a later time period during revision surgery. The disclosed components may also allow a surgeon to reverse/revise a previous motion arthroplasty procedure and/or optionally fuse the joint using more traditional compression methods without requiring removal of the motion-permitting implant components that have already been safely deployed into the body. Desirably, the disclosed systems and methods can address the loss of range of motion in the SI joint from traditional fusion procedures.

BRIEF DESCRIPTION OF THE SEVERAL
VIEWS OF THE DRAWINGS

The foregoing and other features and advantages of the present subject matter will become apparent to those skilled in the art to which the present subject matter relates upon reading the following description with reference to the accompanying drawings.

4

Figures 1A, 1B:
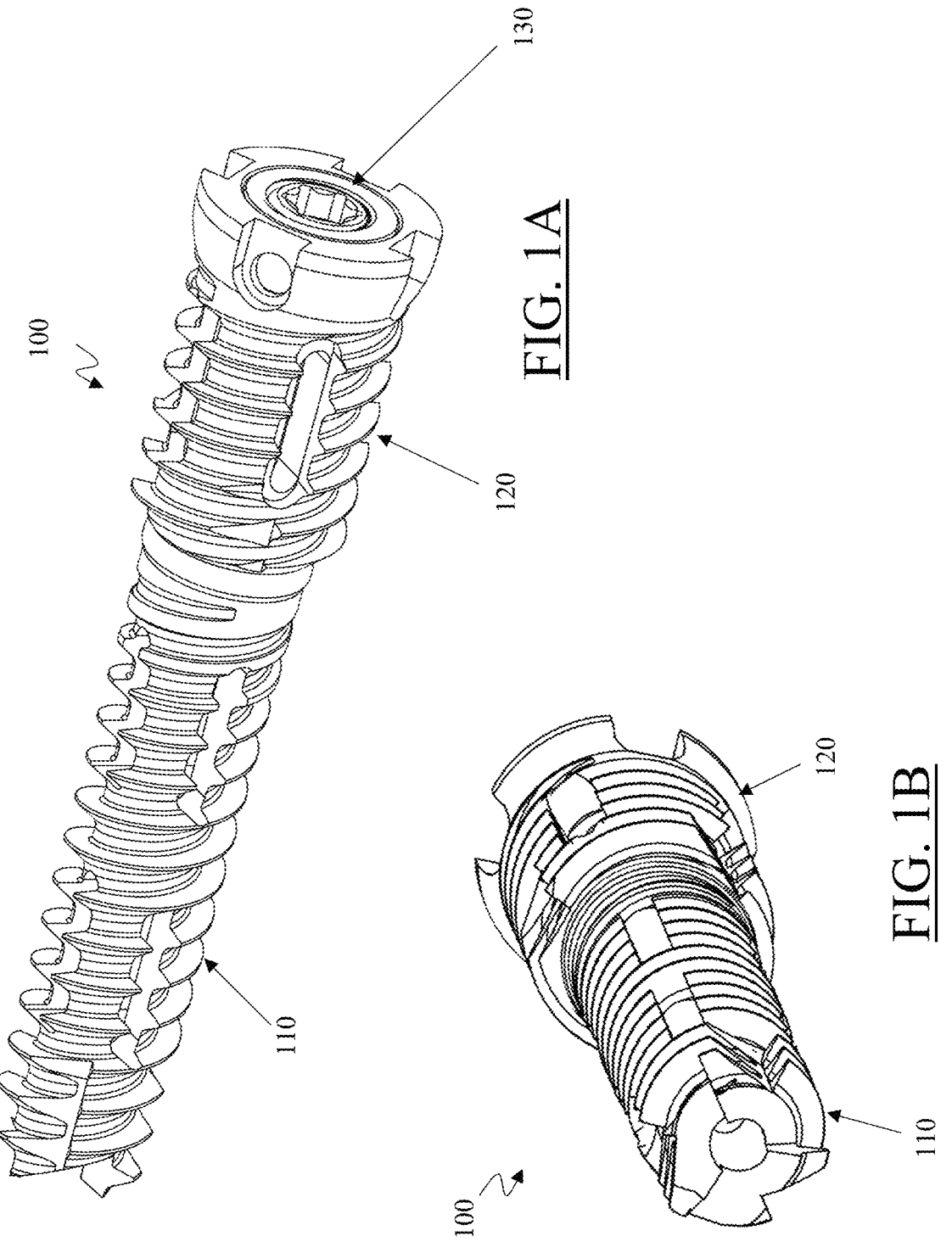
FIGS. 1A and 1B depict various views of one exemplary embodiment of an implant assembly for use in sacral-iliac joint treatment and/or repair.
Figure 6A:
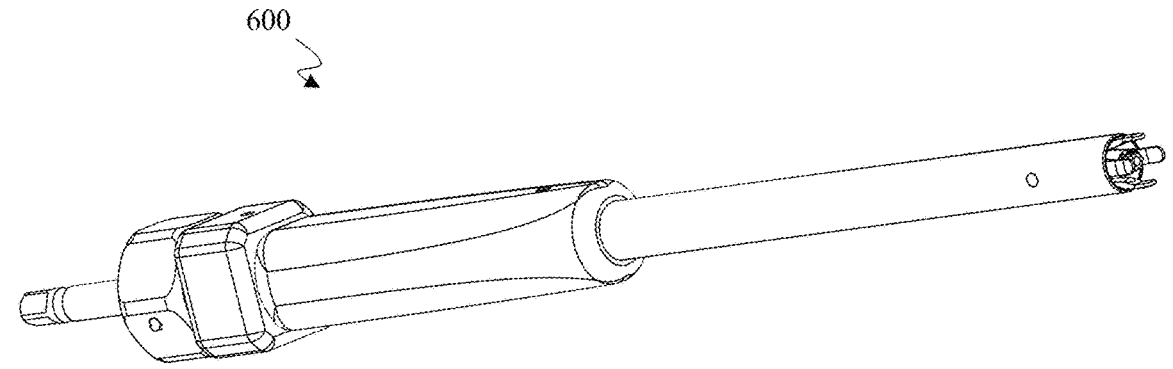
FIG. 6A depicts a perspective view of one exemplary embodiment of an insertion tool.
Figure 6B:
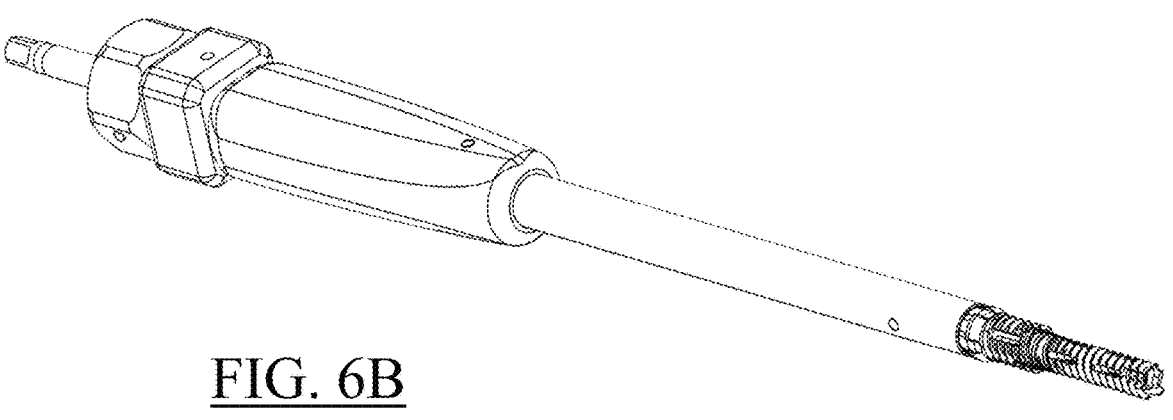
FIG. 6B depicts a perspective view of the insertion tool of FIG. 6A with an attached implant.
Figure 6C:
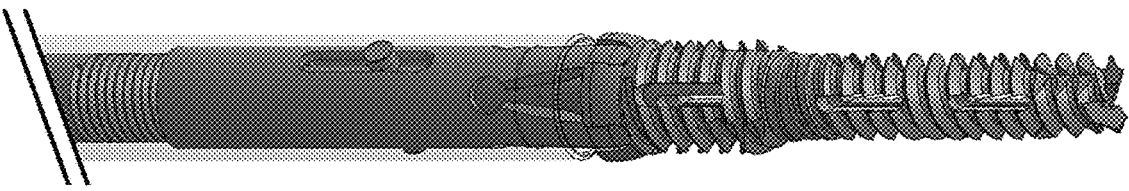
FIG. 6C depicts a partial end view of the insertion tool and attached implant.
Figure 6D:
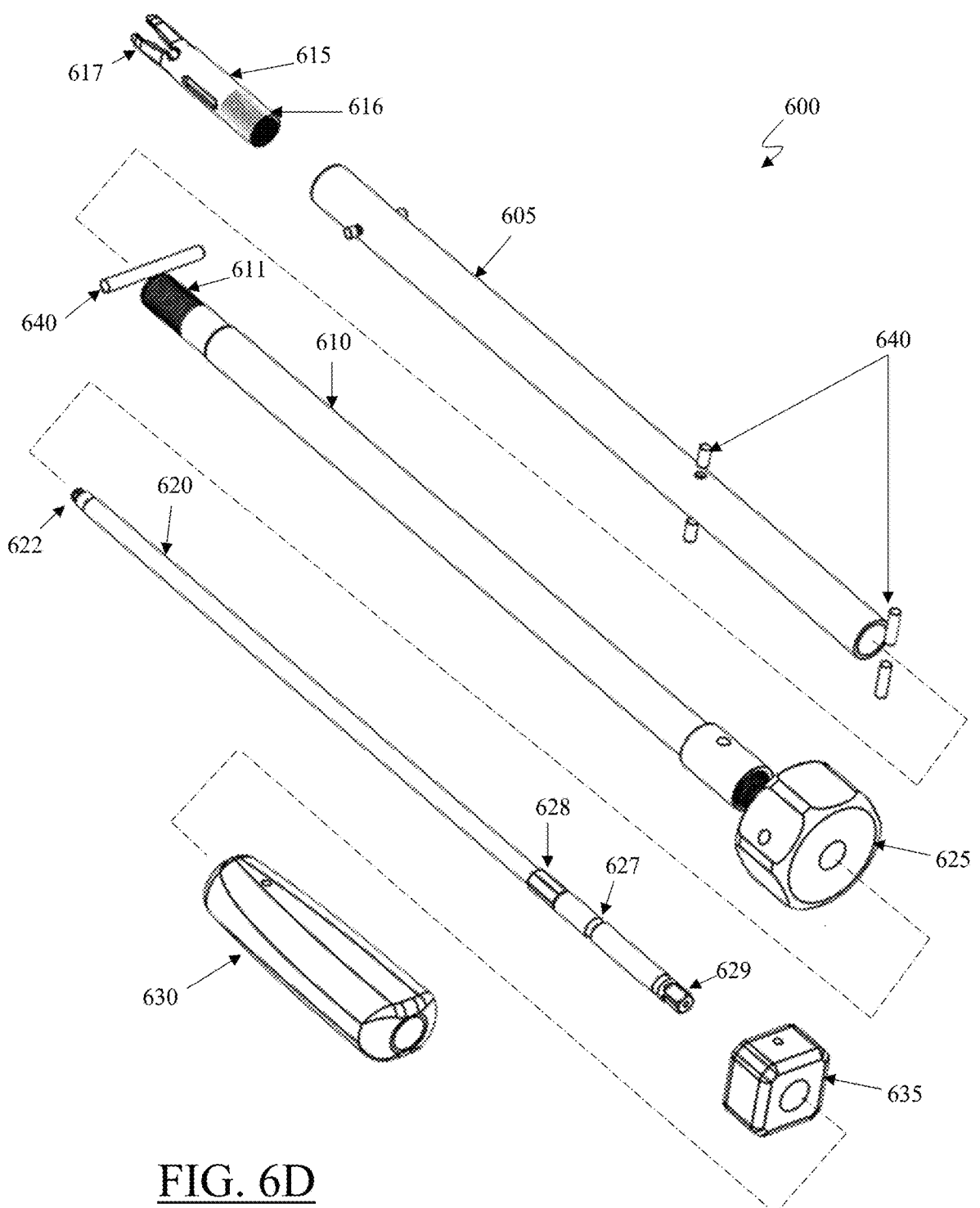
Figure 6E:
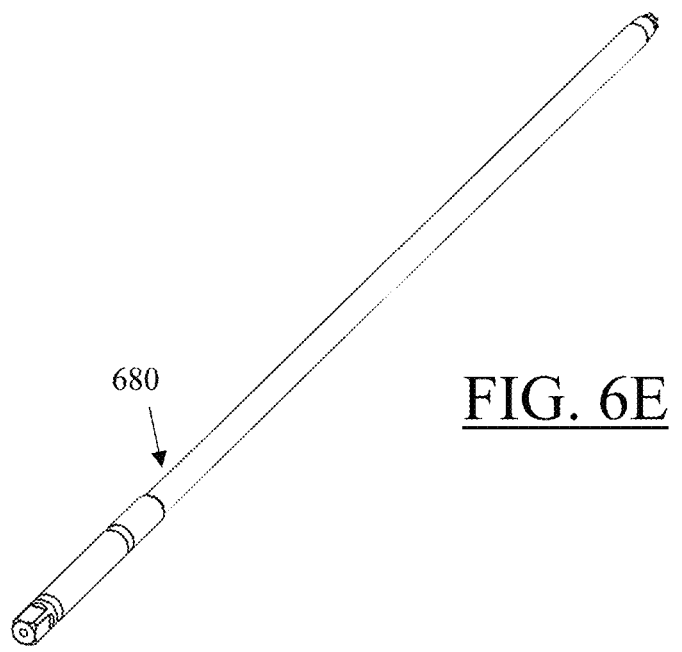
Figure 7A:
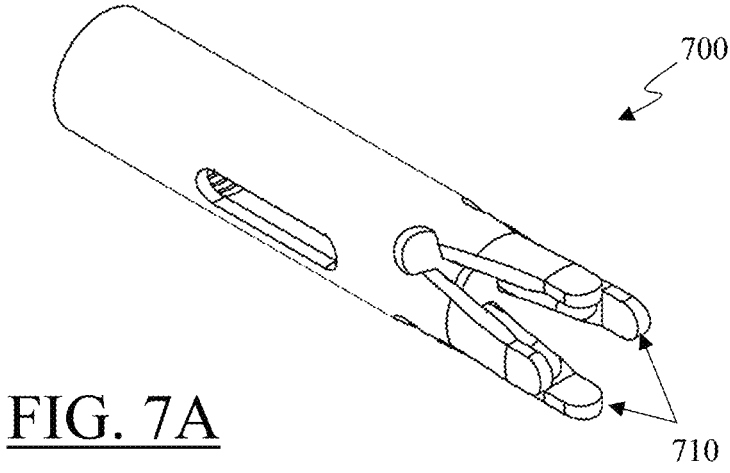
Figure 7B:
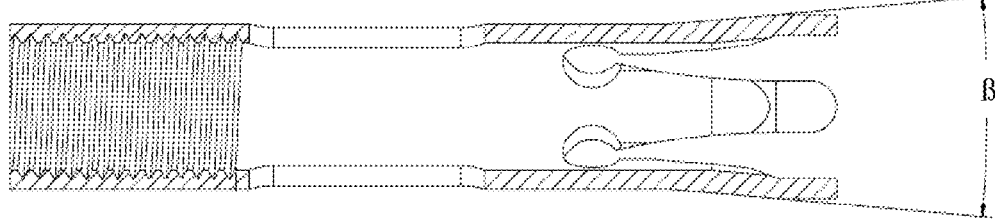
Figure 8A:
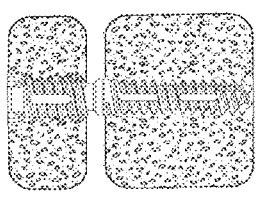
Figure 8A:
Figure 8B:
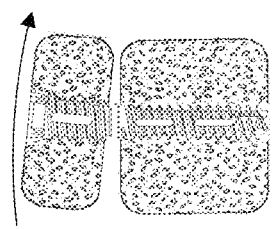
Figure 8C:
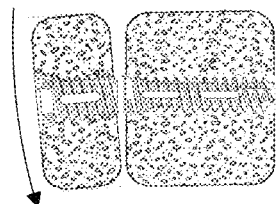
Figure 8D:
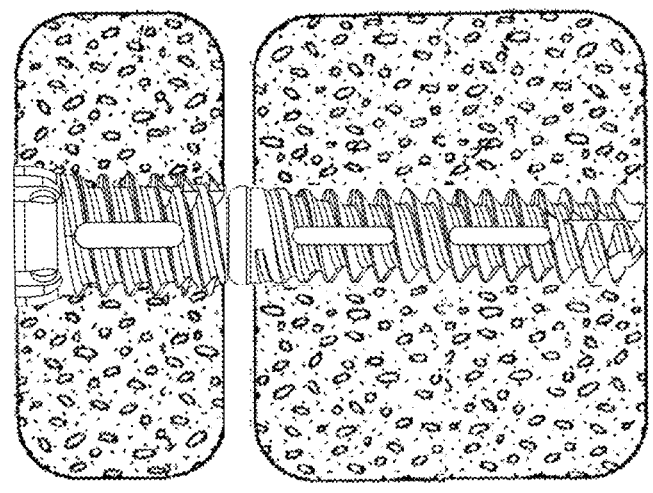
Figure 8E:
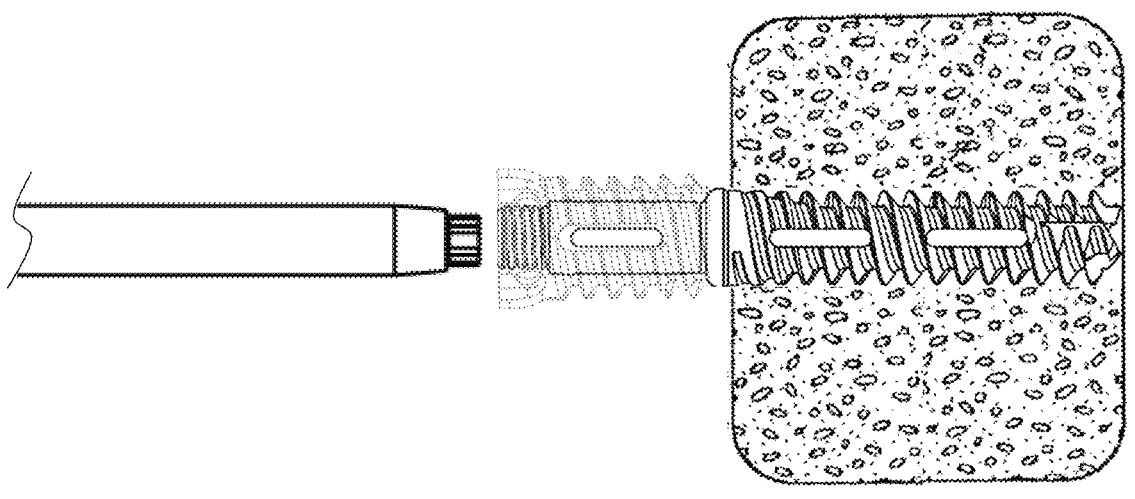
Figure 8F:
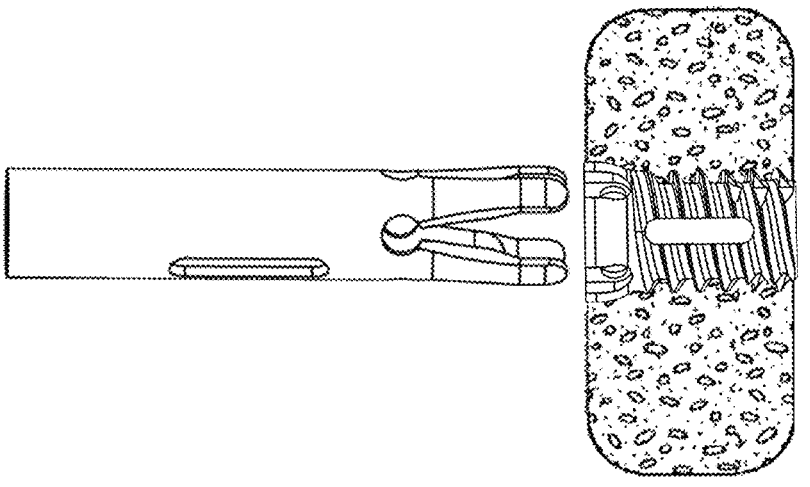
Figure 9A:
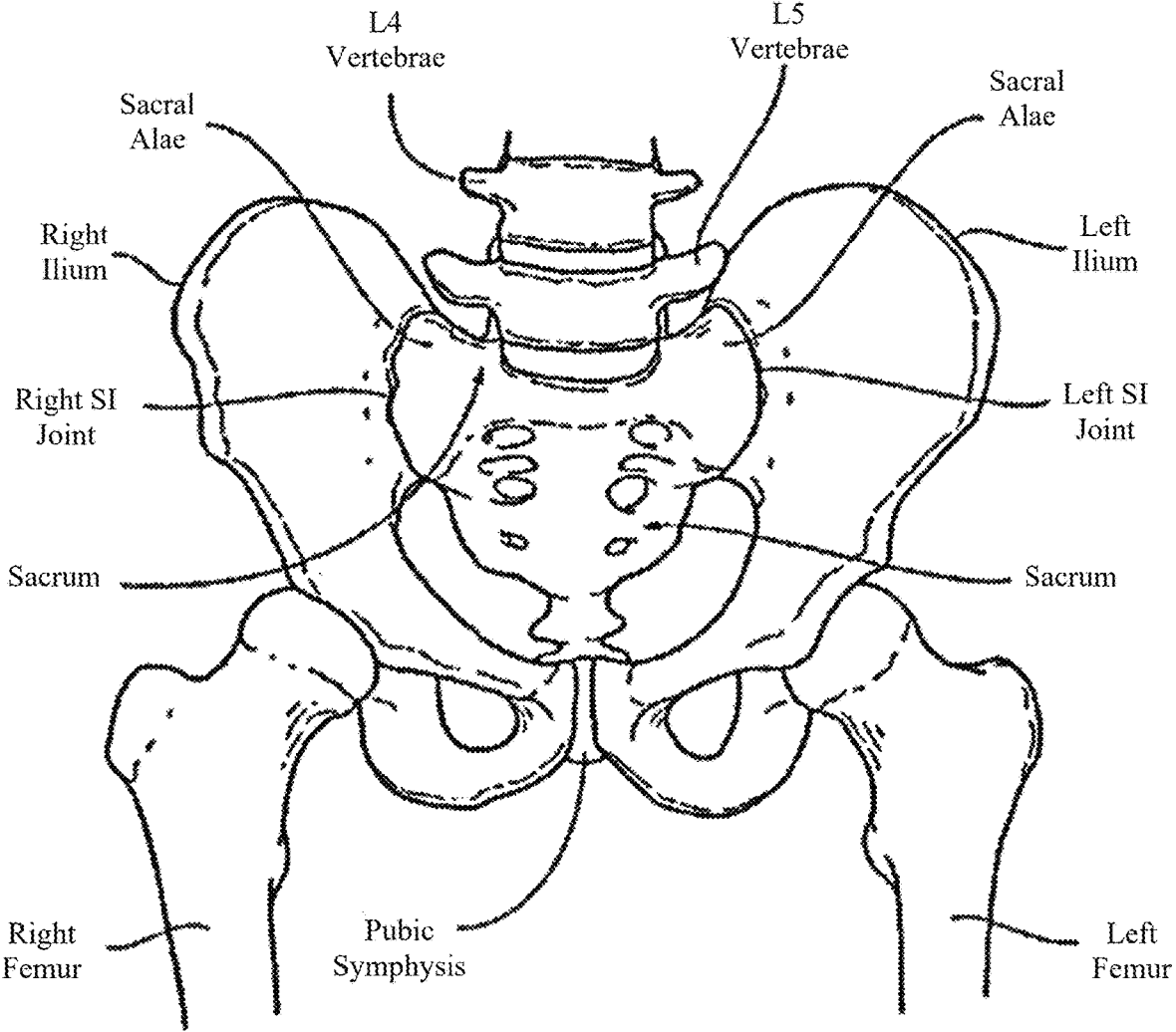
Figure 9B:
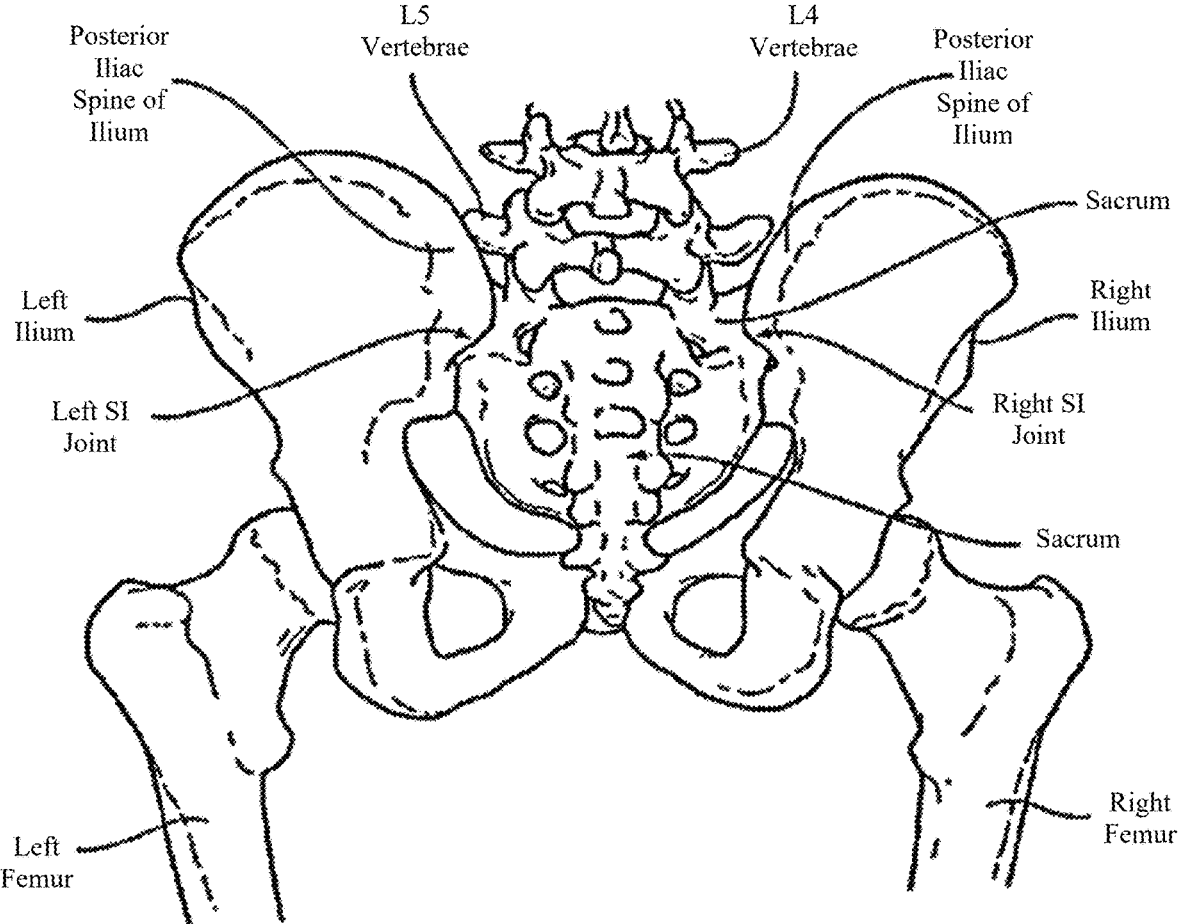
Figure 10A:
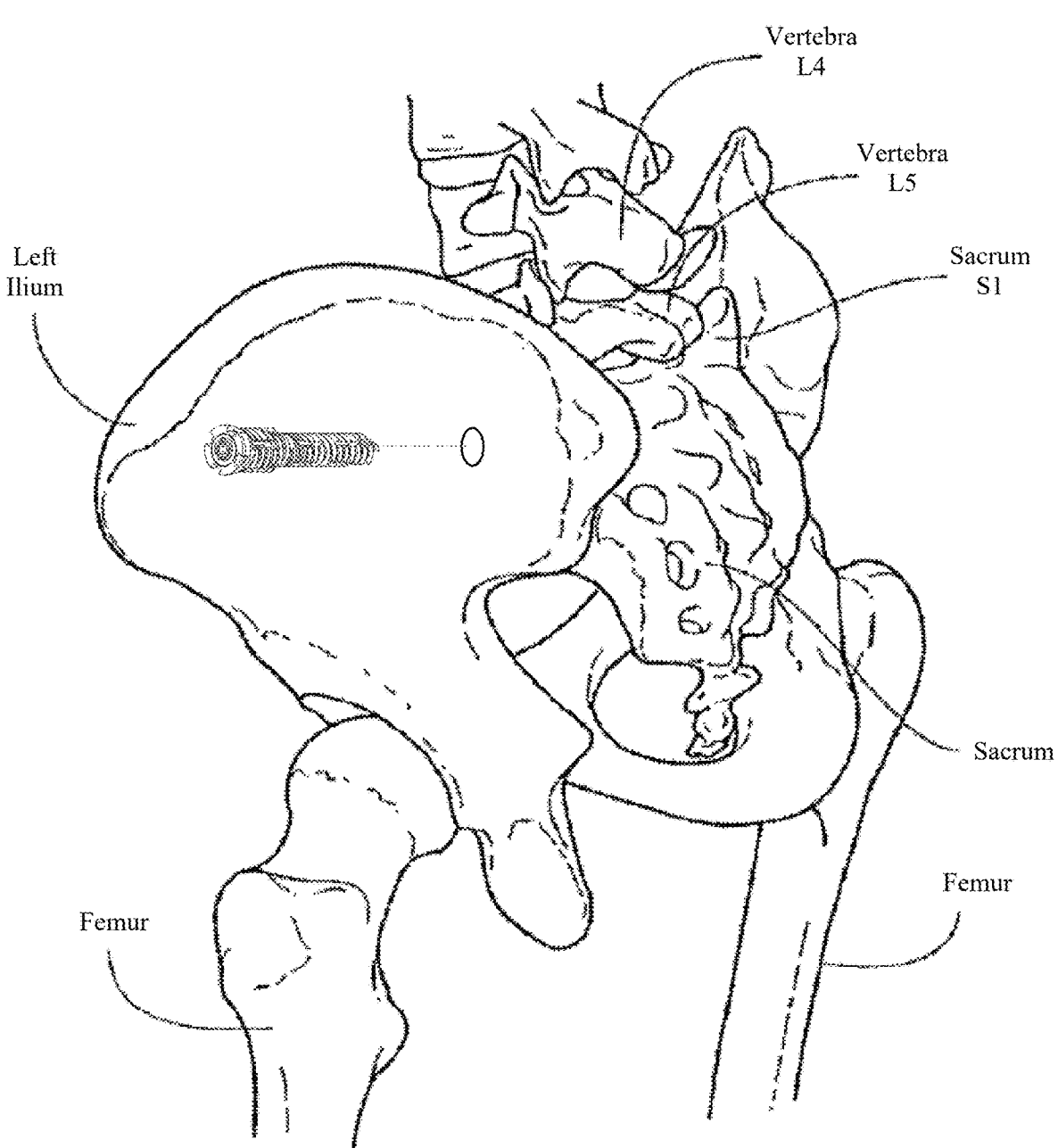
Figure 10B:
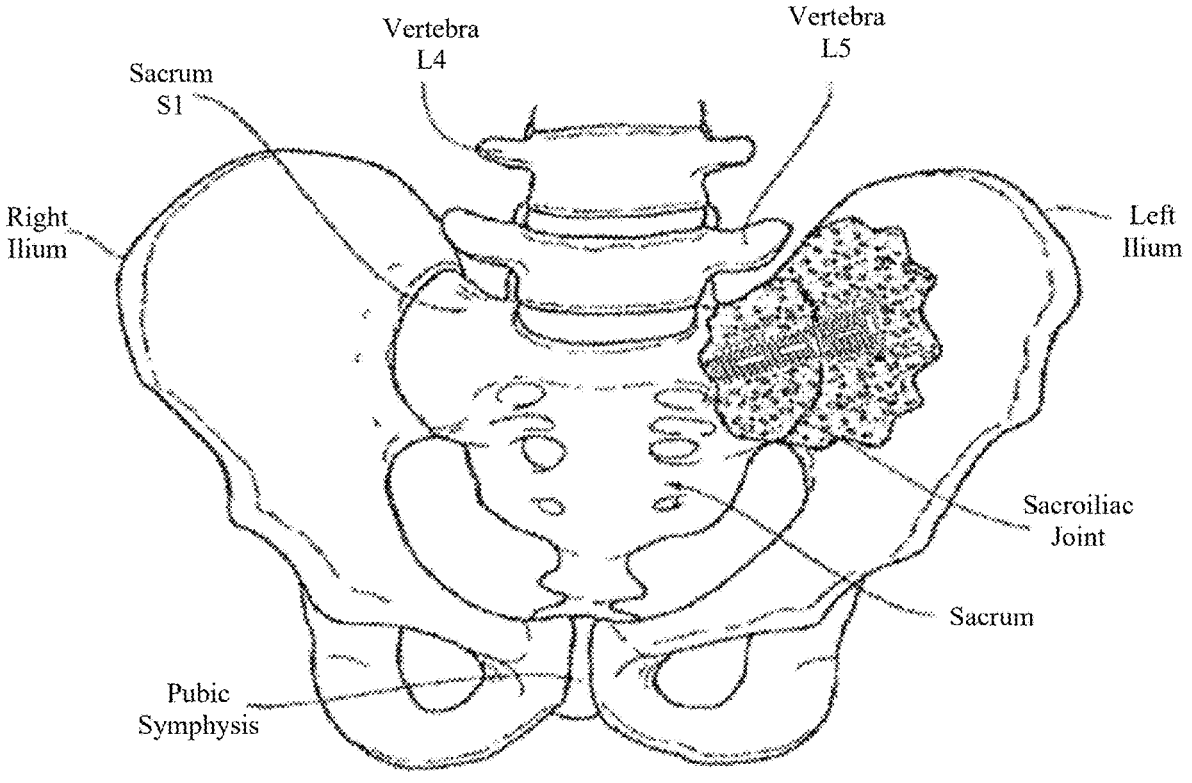
Figure 10C:
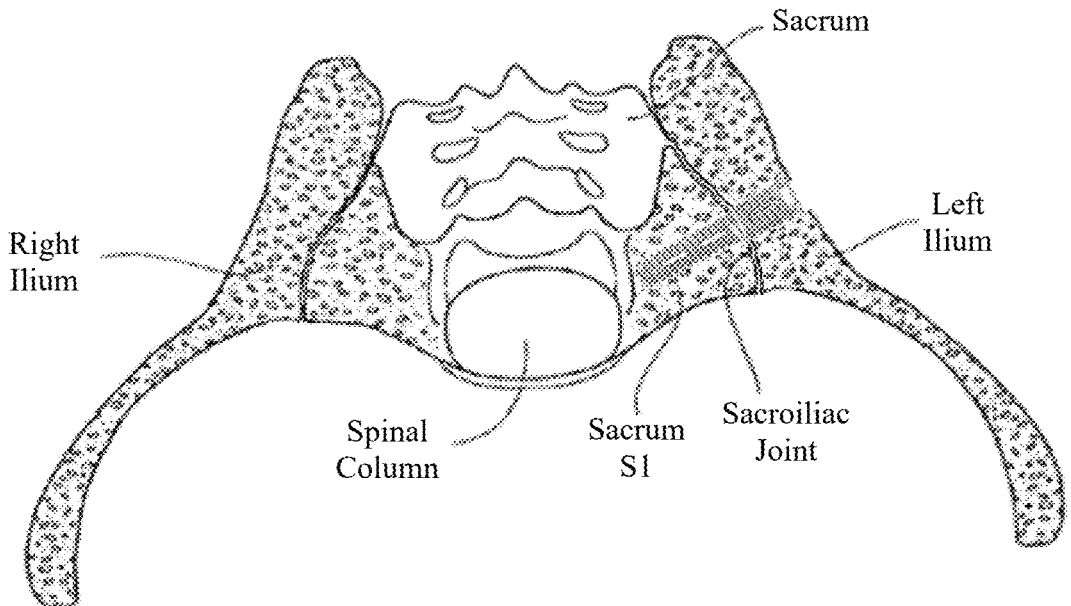
Figure 11A:
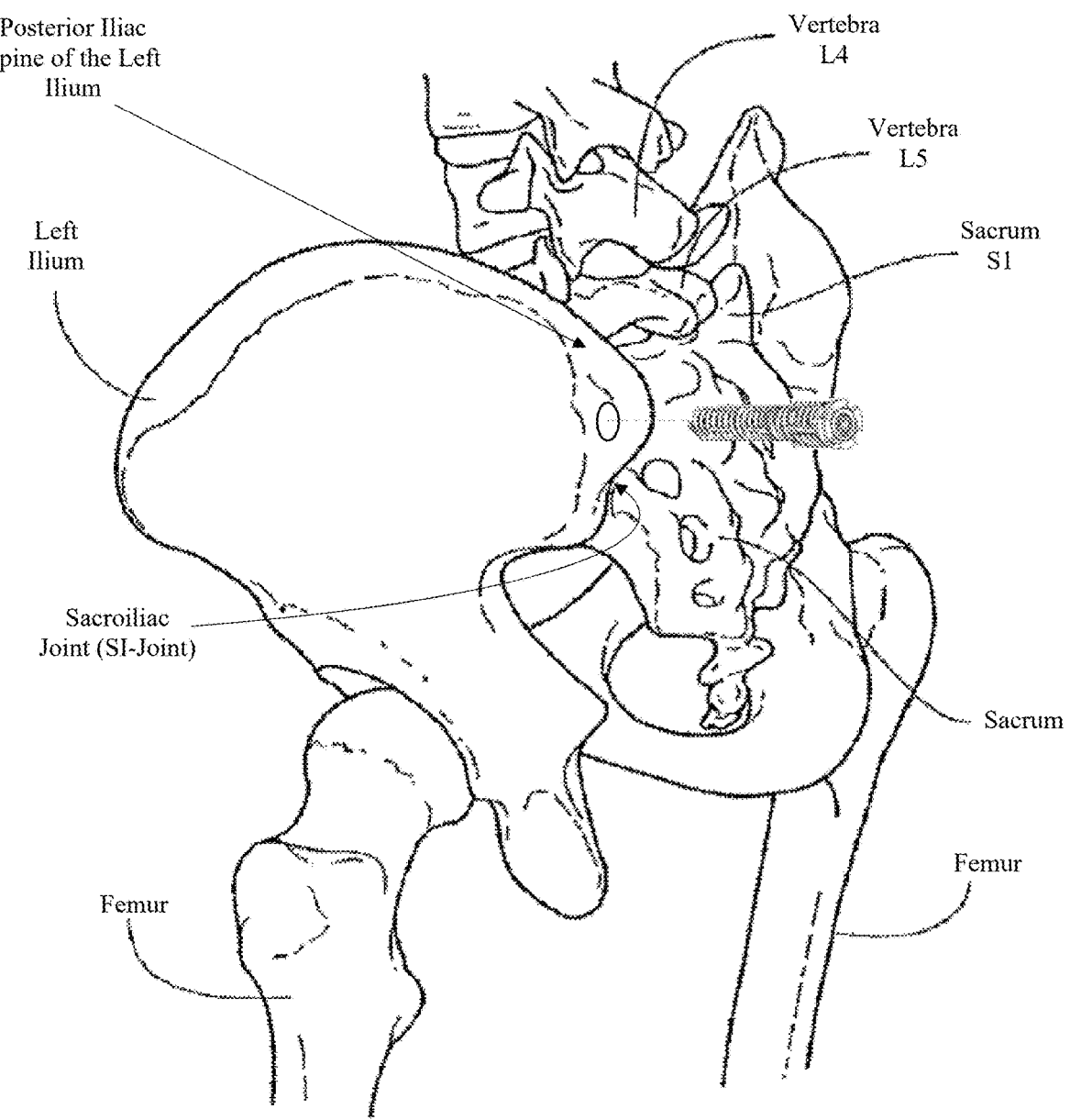
Figure 11B:
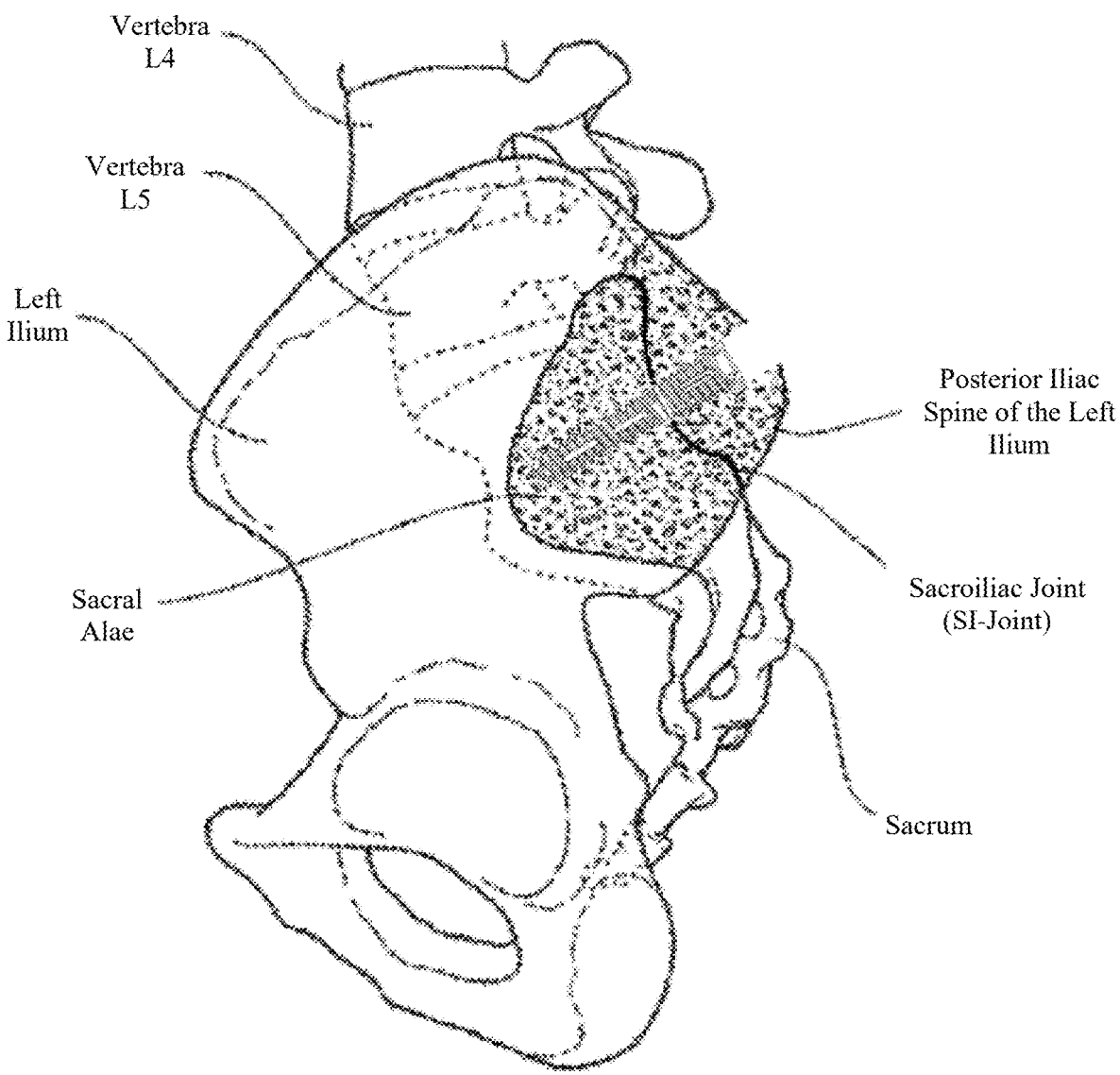
Figure 11C:
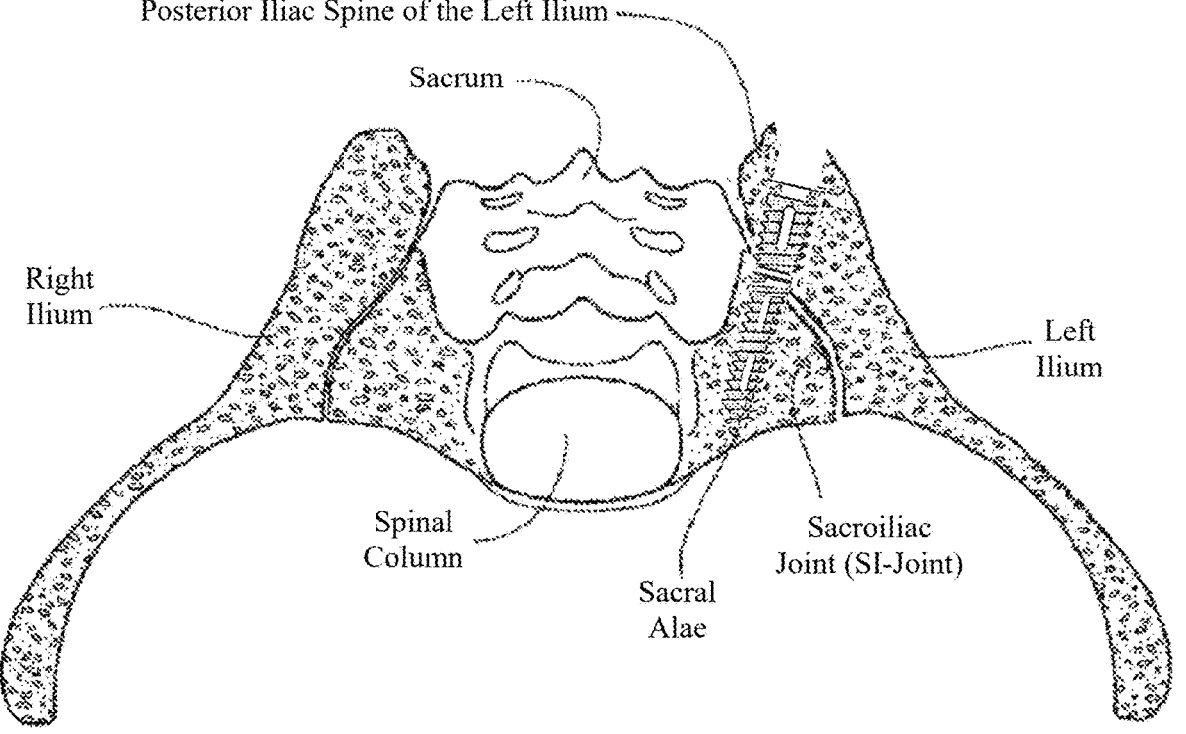
Figure 12A:
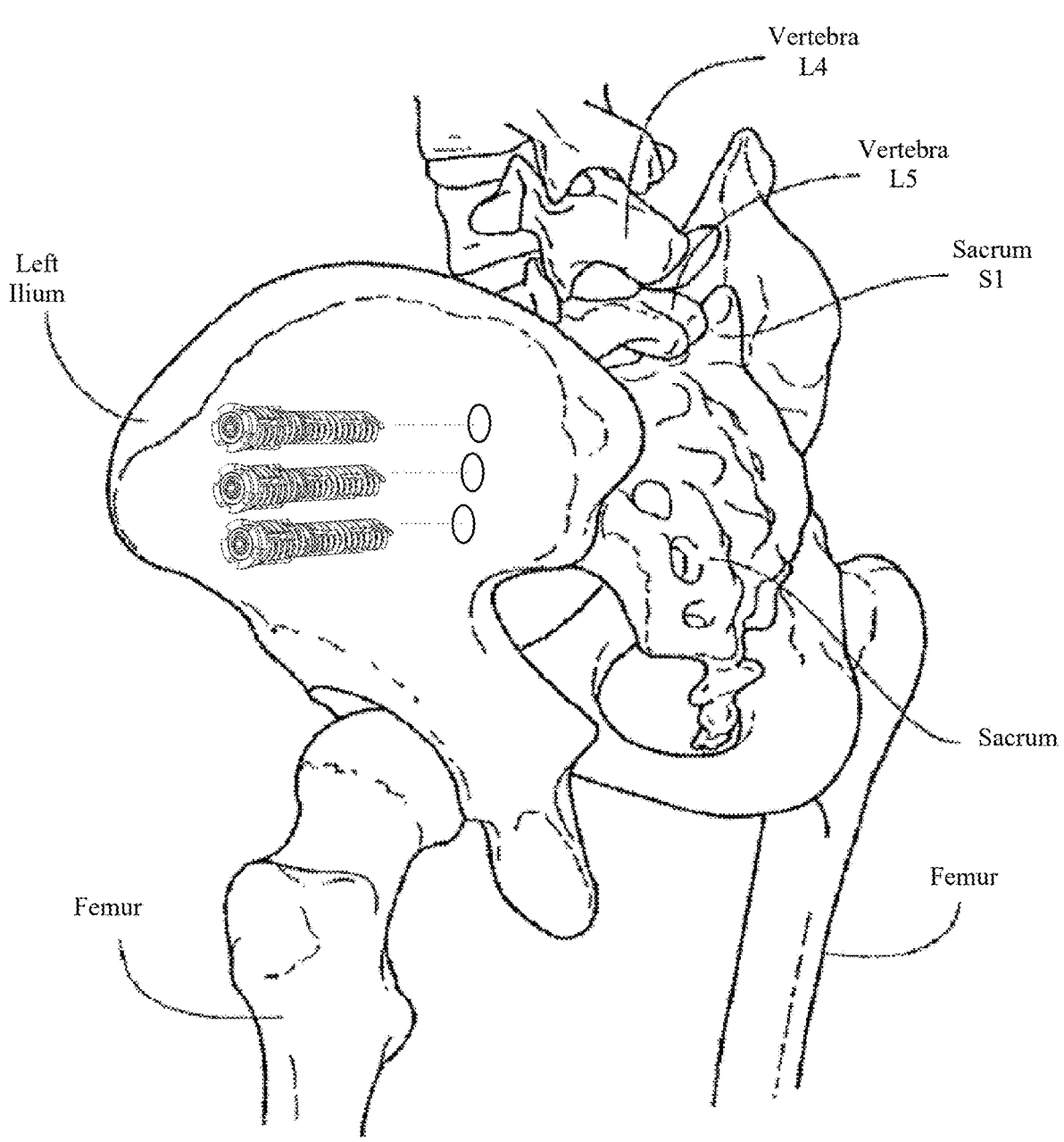
Figure 12B:
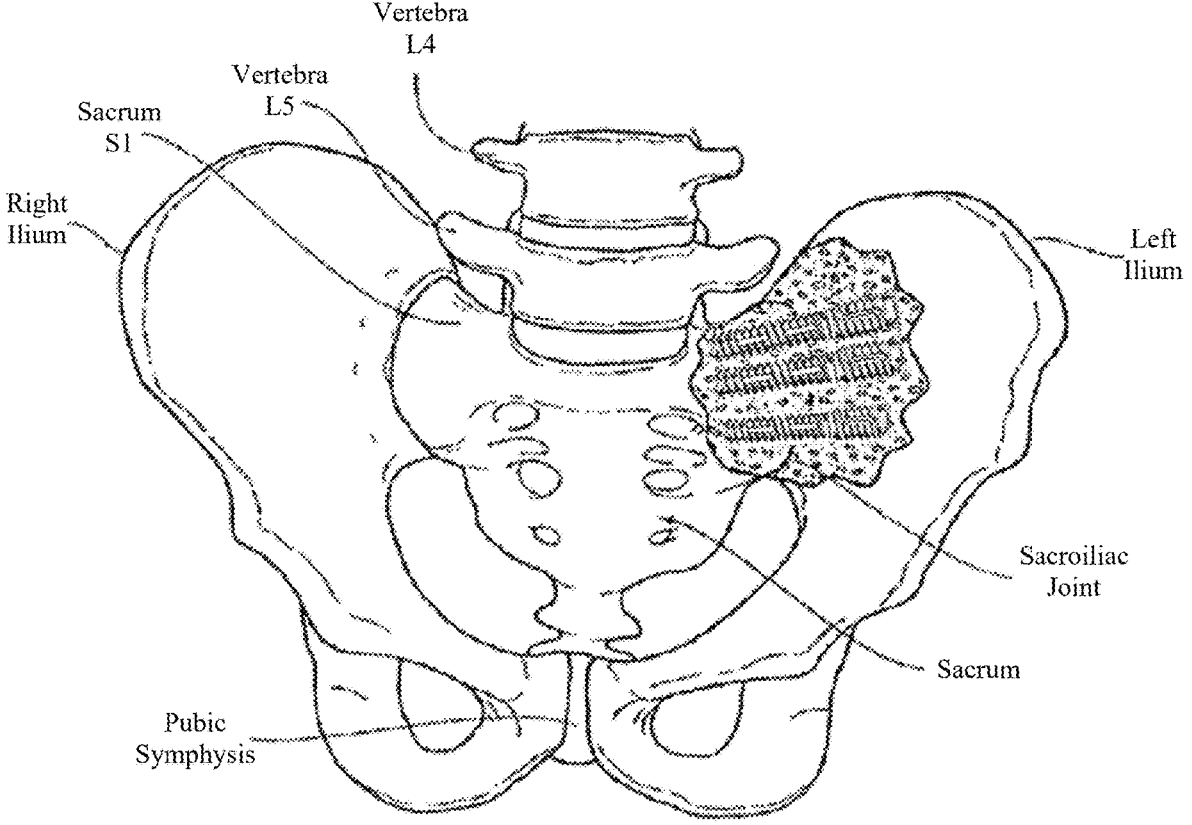

FIG. 6D depicts an exploded view of the insertion tool of FIG. 6A;

FIG. 6E depicts one alternative embodiment of a trim driver shaft body having a rounded and/or smooth outer shaft section;

FIG. 7A depicts a perspective view of one exemplary embodiment of a collet inserter;

FIG. 7B depicts a cross-sectional side view of the collet inserter of FIG. 7A;

FIGS. 8A through 8C depict exemplary movements between a screw body and a threaded axis cage when attached to respective bone surfaces;

FIG. 8D depicts a view of the implant of FIGS. 1A and 1B spanning through a first bone segment or region, through an intervening space or joint, and into a portion of a second bone segment or region;

FIG. 8E depicts a side view of a driving head distal tip engaging with a proximal tip of a screw body;

FIG. 8F depicts a side view of grasping fingers of a collet inserter as they compress, grasp and retain a threaded axis cage portion of an implant;

FIGS. 9A and 9B depict anterior and posterior anatomic views of an exemplary human hip girdle;

FIGS. 10A through 10C depict implantation of the implant of FIGS. 1A and 1B during a sacroiliac arthroplasty procedure via a lateral approach;

FIGS. 11A through 11C depict implantation of the implant of FIGS. 1A and 1B during a sacroiliac arthroplasty procedure via a postero-lateral approach; and FIGS. 12A and 12B depict implantation of one or more implants of FIGS. 1A and 1B during a hip arthroplasty procedure which reduces or immobilizes SI joint motion.

DETAILED DESCRIPTION OF THE
INVENTION

The disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals may represent similar parts throughout the several views of the drawings. In addition, the following is a simplified summary of the subject matter in order to provide a basic understanding of some aspects of the subject matter. This summary is not an extensive overview of the subject matter. It is intended to neither identify key or critical elements of the subject matter nor delineate the scope of the subject matter. Its sole purpose is to present some concepts of the subject matter in a simplified form as a prelude to the more detailed description that is presented later.

In various embodiments, the terms "including," "comprising" and variations thereof, as used in this disclosure, should be interpreted as "including, but not limited to," unless expressly specified otherwise. The terms "a," "an," and "the," as used in this disclosure, mean "one or more," unless expressly specified otherwise.

In some embodiments, devices and/or device components that may be disclosed in communication with each other need not necessarily be in continuous communication with each other, unless expressly specified otherwise. In addition, components that are in direct contact with each other may contact each other directly or indirectly through one or more intermediary articles or devices. The device(s) disclosed herein may comprise various surgical materials, including titanium, titanium alloys, peek, tantalum, chrome cobalt, surgical steel, as well as various other total joint replacement metals and/or ceramics, sintered glass, artificial bone, any uncemented metal or ceramic surfaces, or any other bio-compatible material, and/or any combination(s) thereof.

Although process steps, method steps, or the like, may be described in a sequential order, such processes and methods may be configured in alternate orders. In other words, any sequence or order of steps that may be described does not necessarily indicate a requirement that the steps be performed in that order. The steps of the processes or methods described herein may be performed in any order practical. Further, some steps may be performed simultaneously.

When a single component, device and/or article is described herein, it should be readily apparent that more than one component, device and/or article may be used in place of a single component, device and/or article, unless otherwise noted. Similarly, where more than one component, device and/or article is described herein, it should be readily apparent that a single component, device and/or article may be used in place of the more than one component, device and/or article, unless otherwise noted. The functionality or the features of a component, device and/or article may be alternatively embodied by one or more other components, devices and/or articles which are not explicitly described as having such functionality or features.

Certain exemplary embodiments will now be described to provide an overall understanding of the principles of the structure, function, manufacture, and use of the components, devices and methods disclosed herein. One or more examples of these embodiments are illustrated in the accompanying drawings. Those of ordinary skill in the art will understand that the components, devices and/or methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides various components, devices, systems and methods for treating various anatomical structures of the human pelvis and/or other areas of human and/or animal bodies. While the disclosed embodiments may be particularly well suited for use during surgical procedures for the repair, fixation and/or support of the sacral-iliac joint, it should be understood that various other anatomical locations of the body may benefit from various features of the present invention, including for the repair of bones and for use in, for example, orthopedic surgery and/or bone fracture repair.

In accordance with another aspect of the present subject matter, various methods for manufacturing an implant as set for within any of the details described with the present application are provided.

In at least one exemplary aspect, the invention further provides for a surgical method for stabilizing the sacral-iliac joint between an iliac and a sacrum. The method comprises creating an insertion path through the ilium, through the sacral-iliac joint, and into the sacrum or other vertebral bodies/structures. The method includes providing a screw body sized and configured to be introduced through an insertion path laterally into the ilium and sacrum. The screw body has a distal end sized and configured to be located in an interior region of the sacrum or other bone; a proximal end sized and configured to be located outside of the sacrum/bone (and extending into/through a corresponding threaded axis cage anchored in the ilium); and an articulating region sized and configured to span the sacral-iliac joint. The method includes providing an elongated implant structure sized and configured to span the sacral-iliac joint between the iliac and sacrum. The method includes introducing the screw body through the insertion path from the ilium, through the sacral-iliac joint, and into the sacrum. The method includes anchoring the distal end of the screw body in the interior region of the sacrum. The method includes anchoring the threaded axis cage into the ilium, with a mid-point and/or proximal portion of the screw body spanning the sacral-iliac joint between the ilium and sacrum. A locking nut can then be secured to a distal end of the screw body, which secures the screw body to the threaded axis cage, desirably stabilizing the sacrum and ilium relative to each other. Depending upon the compressive force provided by the nut, one or more articulating surfaces between the screw body and the threaded axis cage can desirably allow a controlled amount of motion to occur between the sacrum and the ilium while preserving a desired separation between these bony structures (e.g., a smaller outer diameter of the locking nut can allow increased clearance between the nut and the lumen of the widened section of the threaded axis cage, thereby permitting more movement of the cage relative to the screw). If desired, the locking nut may form a separate and/or replaceable component of the system, and may be provided in various outer diameters and/or sizes in a kit of implant components of differing sizes and/or configurations. Alternatively, the locking nut may be permanently connected to the screw body by welding, adhesives and/or other locking mechanisms, such as where the implant may be provided in a fully-assembled fashion (e.g., preassembled) for use in surgery.

In various embodiments, the cage inner diameter and/or the locking nut outer diameter may be selected, configured and/or altered in varying combinations to obtain a desired and/or adequate range of motion for the device. Similarly, the cage inner diameter and/or the locking nut outer diameter may be selected, configured and/or altered in varying combinations to obtain a desired limit (or limits) to the range of motion provided by the device.

In other embodiments, a significantly greater compressive force may provided by the nut in an attempt to minimize and/or immobilize the articulating surfaces, thereby reducing and/or eliminating joint motion in a desired manner, such as where the implant is being utilized as a fusion construct.

Figure 2:
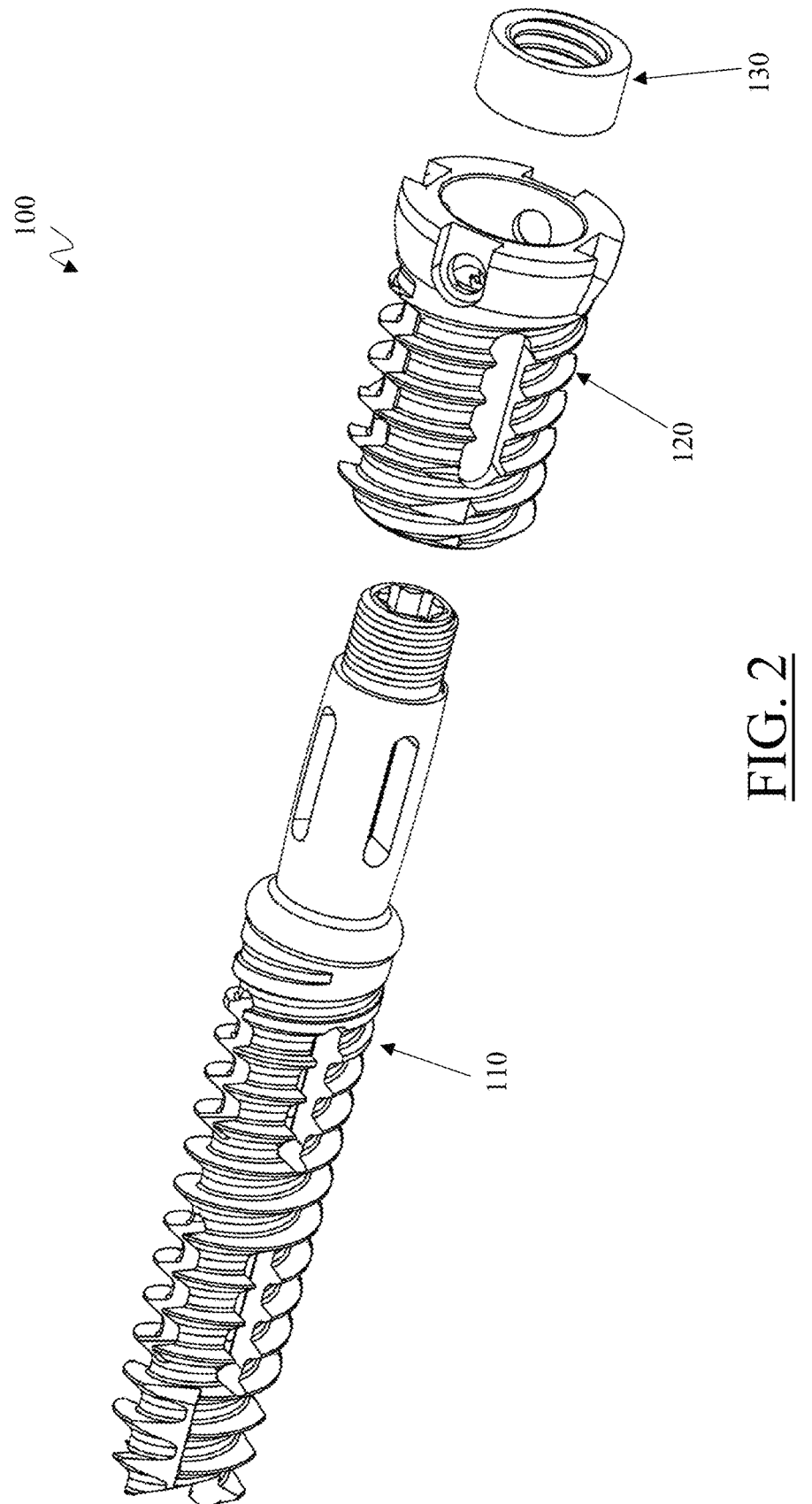
FIG. 2 depicts and exploded view of the implant assembly of FIGS. 1A and 1B.

FIGS. 1A, 1B and 2 depict assembled and exploded views of one exemplary embodiment of an implant assembly 100 for use in sacral-iliac joint treatment and/or repair. In this embodiment, the implant 100 comprises a screw body 110, a threaded axis cage 120 and a locking nut 130, which are desirably sized and configured for the stabilization of bones (i.e. stabilization of two or more individual bones that are adjacent and/or jointed).

In use, the implant 100 is desirably sized to span a distance through one adjacent bone segment or region, through the intervening space or joint, and into at least a portion of the other adjacent bone segment or region, such as depicted in FIG. 8D. The implant 100 can be sized based on length and diameter according to the local anatomy. The morphology of the local structures can be generally understood by medical professionals using textbooks of human skeletal anatomy along with their knowledge of the site and its disease or injury. The physician is also able to ascertain the desired dimensions and/or allowable ranges thereof of the implant 100 based upon prior analysis of the morphology of the targeted bone region using, for example, plain film x-ray, fluoroscopic x-ray, or MRI or CT scanning. One representative diameter for the implant 100 can range between 11 mm to 14 mm.

As best shown in FIG. 2, at least the distal portion of the screw body 110 and substantially all of the threaded axis cage 120 can include external helical ridges or screw threads formed around their body exteriors. If desired, the shape, size, distribution and/or direction of these screw threads can be different, or they can be the same—e.g., they can desirably comprise right-hand threads in one exemplary embodiment. The screw body and/or axis cage may incorporate aggressive buttress bony single, double or triple lead threads that match in pitch for unified insertion of the screw and cage through the SI joint using the disclosed insertion tools. In various alternative embodiments, different sizes, shapes, distributions and/or directions of threads may be employed.

If desired, the thread patterns for an implant may vary based on side of patient being treated, such as a left handed threaded implant for one side of the patient and a right handed threaded implant for the opposing side. In other embodiments, the implant could incorporate a screw body having a right handed thread and a threaded cage body having a left handed screw, which would desirably be implanted using independent rotation for each component, with the resulting implant being highly resistant to unwanted migration and/or backing out.

It should be understood that the implant components can take various shapes and have various cross-sectional geometries. The implant can have, e.g., a generally cylindrical and/or curvilinear (i.e., round or oval) cross-section. Other alternative shapes such as a generally rectilinear cross section (i.e., square or rectangular or triangular, or combinations thereof) are possible. Where the implant structure is non-curvilinear in cross section, it may more effectively resist rotation and/or micromotion once implanted. Similarly, the implant can include one or more tapered regions at least along a portion of its axial length, meaning that the width or diameter of the implant structure may increase and/or decrease along its axial length. In one exemplary embodiment, a tapered region may correspond with, in use, a proximal region of the implant (i.e., the last part of the implant to enter bone). The amount of the increase/decrease in width or diameter can vary.

The disclosed implant system, tools and procedures are desirably employed during a surgical procedure for treatment of a sacro-iliac joint of a patient. Alternatively, the implant system may also be employed with other surgical procedures. In particular, the disclosed implant system is employed with a surgical arthroplasty procedure for treatment of an applicable condition or injury of an affected sacro-iliac joint. It is contemplated that the implant system is inserted into a sacro-iliac joint to desirably space apart articular joint surfaces, establish joint tension, provide support and allow for relative motion of the articular surfaces of the sacro-iliac joint in a less invasive approach for treatment. It is further contemplated that the implant system is inserted to achieve benefits similar to those of existing sacro-iliac joint spacers such as restoring ligamentous tension, eliminating painful motion, as well as to preserve and restore motion and/or separate and cushion opposing articulating surfaces. It is envisioned that the implant system may maintain joint motion and/or tension without or with promoting bone growth within the joint. For example, where joint motion may be retained and/or desired, bone ingrowth across the joint may not be preferred and is desirably inhibited by the implant design and joint motion allowed therein. Alternatively, where limited and/or no motion may be desired, then bone growth across the joint could be encouraged with the introduction of osteo-inductive and/or osteoconductive materials.

Figure 3A:
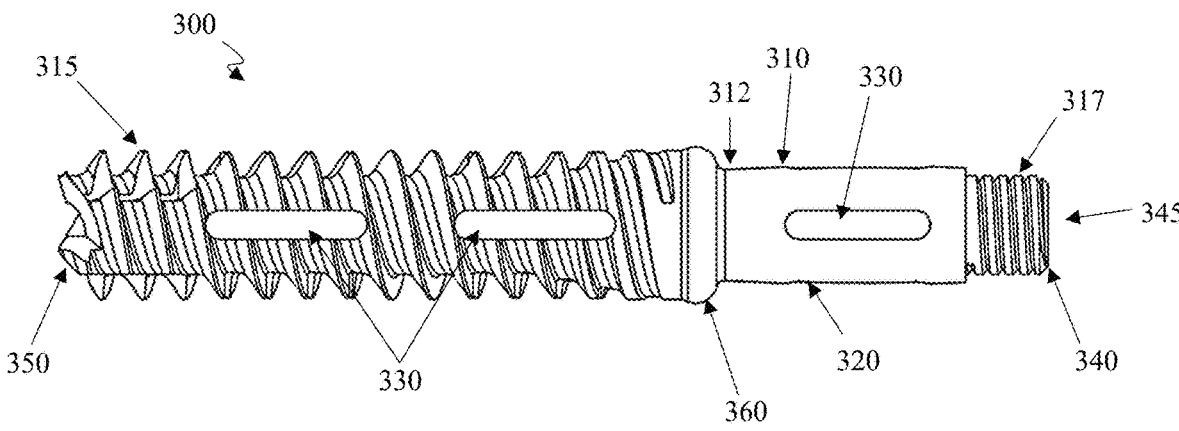
FIGS. 3A and 3B depict views of one exemplary embodiment of a screw body.
Figure 3B:
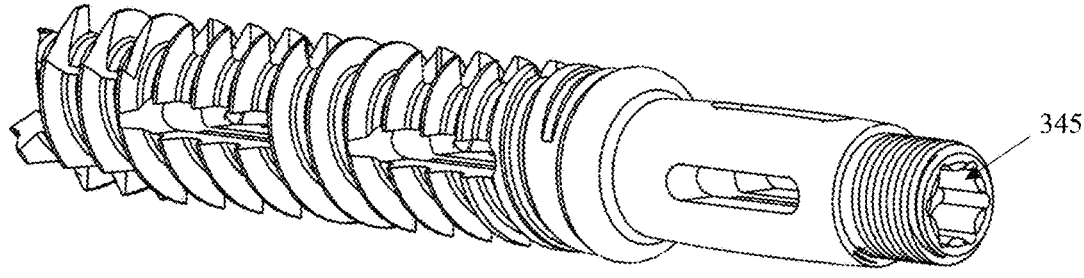

FIGS. 3A and 3B depict views of one exemplary embodiment of a screw body 300, which includes an elongated generally cylindrical body 310 having a distal set of external threads 315, a proximal set of external threads 317 and generally smooth rounded section 320. The body 310 also includes a series of body openings 330 extending therethrough. The body 310 having proximal end 340 with a driving section 345, a distal end 350 and a rounded or curved articulating surface 360 positioned proximate to the smooth rounded section 320. The screw body 300 can be cannulated to allow for the implant to be inserted with a guidewire.

Figure 3C:
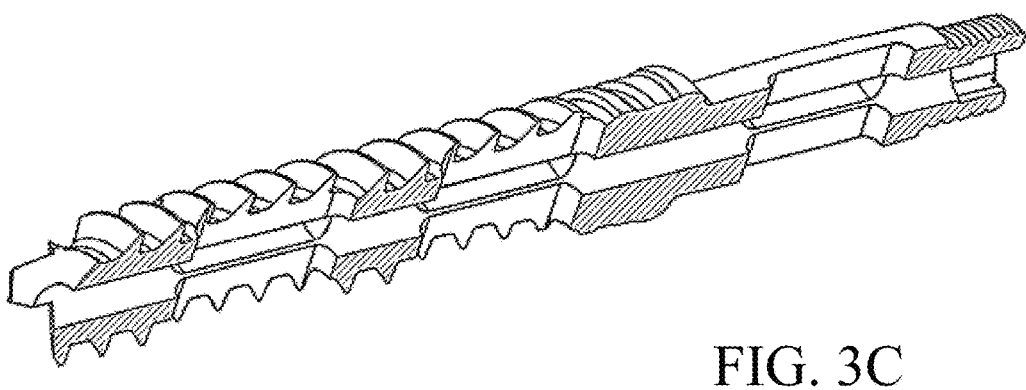
FIG. 3C depicts a cross-sectional view of the screw body of FIGS. 3A and 3B.

As best seen in FIG. 3B, the driving section 345 of the screw body incorporates a torque attachment point for the inserter, which allows the threaded axis cage and the screw body to be operated independently (e.g., individually rotated) and/or operated in unison, at the surgeon's option. FIG. 3C depicts a cross-sectional view of the screw body 300.

The screw body can be fenestrated to allow for bony on growth, and in various embodiments the screw body can incorporate a self-cutting, self-tapping and/or non-tapping tip. If desired, the bone screw and/or threaded axis cage can either or both have self-tapping tips that allows the implant to be installed without need for a pilot hole, and self-harvesting geometry that gathers and retains bone shavings in and along the bone screw and/or cage/sleeve that are produced by component installation for use as graft for fusing the bones to the implant.

In one exemplary embodiment, a set or kit of implants can be provided. The screw body can be provided in implant lengths which vary from 10 mm to 180 mm in increments of 5 mm (but can have smaller increments in other embodiments). Minor diameters of the screw body can be provided which vary from 2 to 20 mm in 1 mm increments.

Figure 4A:
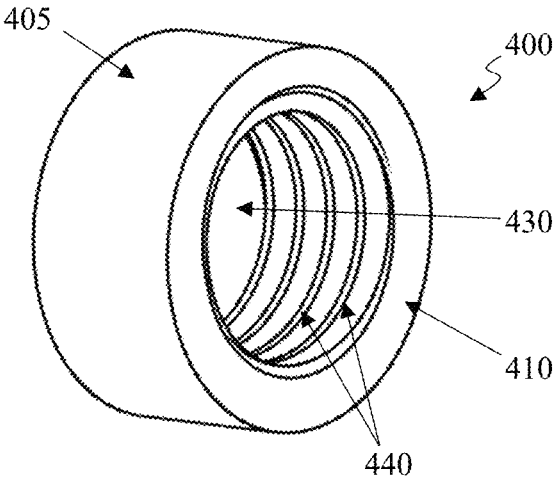
FIGS. 4A and 4B depict views of one exemplary embodiment of a collet or nut.
Figure 4B:
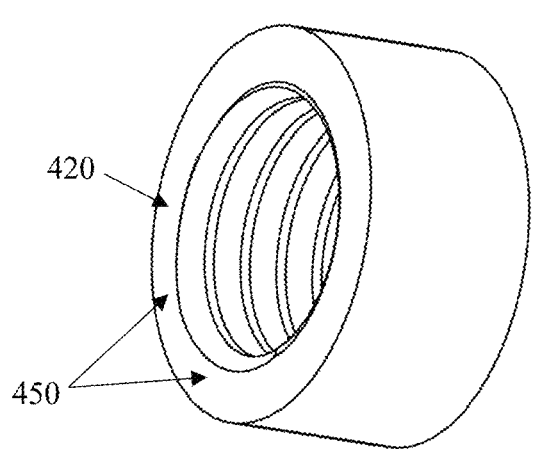
Figure 4C:
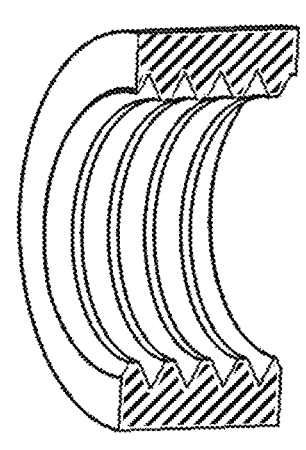
FIG. 4C depicts a cross-sectional view of the collet or nut of FIGS. 4A and 4B.

FIGS. 4A and 4B depict views of one exemplary embodiment of a collet or nut 400 having a generally cylindrical body 405, a proximal end 410, a distal end 420, and a central bore 430 having internal threads 440. The distal end of the nut 400 desirably includes a generally smooth, flattened surface 450. FIG. 4C depicts a cross-sectional view of the nut 400.

In various embodiments, the locking nut may be optionally laser welded or otherwise permanently secured to the screw body to secure the threaded cage onto the screw body creating the screw assembly (e.g., where the implant may be provided to a surgeon in a fully assembled fashion). In alternative embodiments, the locking nut may be removeable and/or the components of the implant assembly may be provided in a modular fashion and assembled prior to and/or during a surgical procedure.

Figures 5A, 5B, 5C:
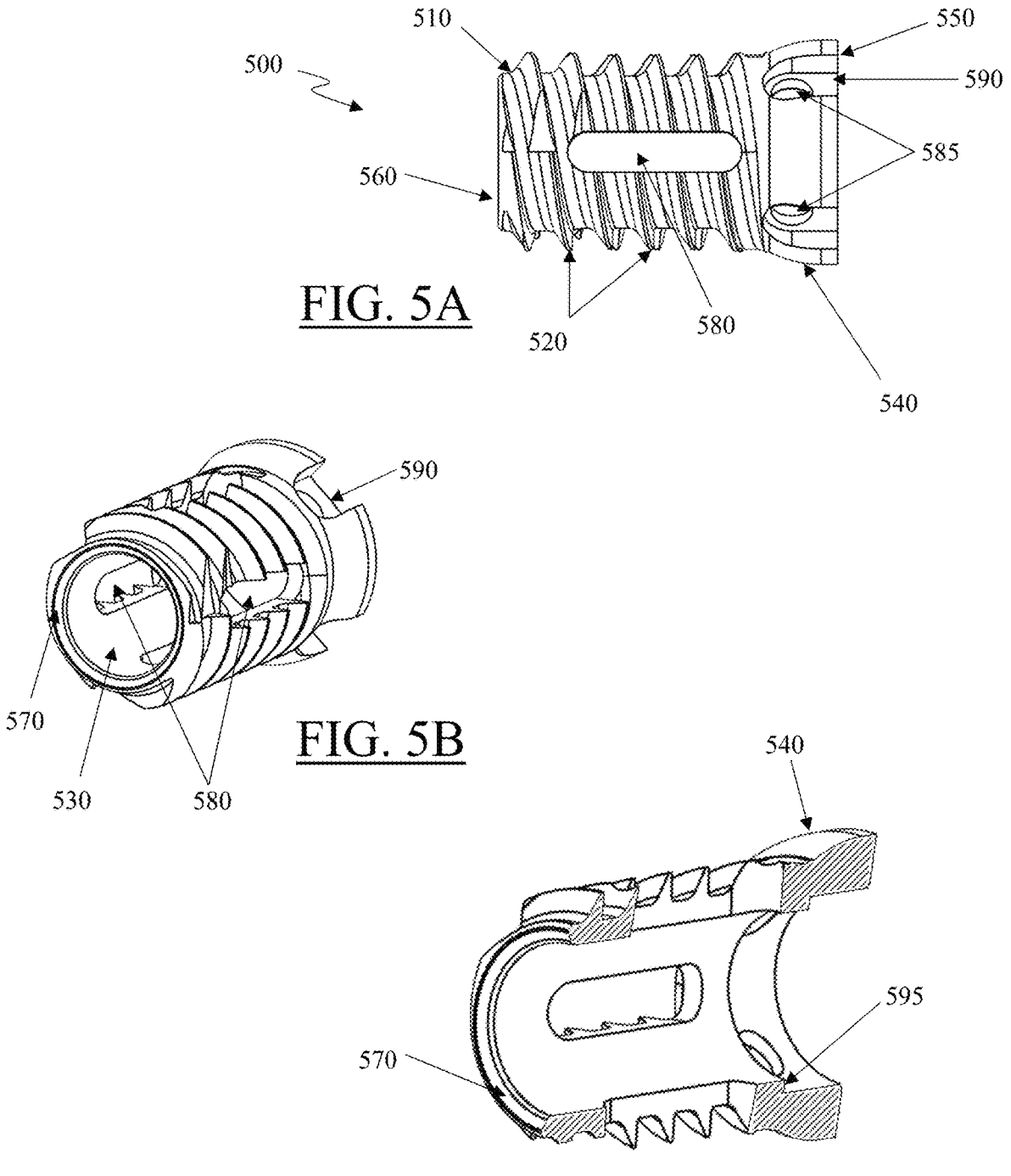
FIGS. 5A and 5B depict views of one exemplary embodiment of a threaded axis cage.
FIG. 5C depicts a cross-sectional view of the threaded axis cage of FIGS. 5A and 5B.

FIGS. 5A and 5B depict views of one exemplary embodiment of a threaded axis cage 500, which includes a generally cylindrical body 510 having external threads 520 with a central opening or lumen 530 extending therethrough, with a widened section 540 near a proximal end 550 of the body 510. As best seen in FIG. 5B, an articulating surface 570 is formed on a distal end 560 of the body 510. In addition, the body includes a series of first openings 580 and second openings 585 extending through the body 510 (e.g., from the threaded external surface to the lumen 530), with a set of notches or detents 590 positioned on an outer surface of the widened section 540 and opening towards the proximal end 550 of the body 510. Desirably, the notches and detents 590 and/or second openings 585 can accommodate an inserter and/or driving tool (See FIG. 8F) which allows independent rotation and/or manipulation of the cage, if desired. FIG. 5C depicts a cross-sectional view of the threaded axis cage 500.

As best seen in FIG. 5C, the widened section 540 or "head" of the threaded axis cage further incorporates an internal shoulder surface 595 which can serve as a buttress and/or articulation surface which interacts with the flattened end surface 450 of the nut or collet, wherein the nut attaches to the screw body to retain the threaded axis cage thereon. The distal end 560 or base of the threaded axis cage can include one or more articulating surfaces 570 (e.g., a concave articulation in this figure) to create a sliding ball joint between the threaded axis cage and the rounded or curved articulating surface 360 of the screw body, thereby allowing for movement between the threaded axis cage 500 and the screw body 300 to create a range of motion within the joint while concurrently providing stabilization of the attached bone structures. The clearance between the inner diameter of lumen 530 (within the threaded axis cage 500) and the outer diameter of the generally smooth rounded section 320 (of the screw body 300) can allow for movement between the threaded axis cage 500 and the screw body 300, and thus a range of motion between these two structures, which can potentially be from 0 to 20 degrees of relative movement therebetween. The threaded axis cage lengths can vary from 5 mm to 120 mm.

Desirably, the internal threads 440 of the nut 400 are desirably sized and configured to accommodate an engage with the proximal set of external threads 317 of the screw body 300, with the threaded axis cage sandwiched between the screw body 300 and the nut 400 in the assembled implant.

In embodiments where the collet or nut maybe selectively tightened and/or loosened on the screw (e.g., where the nut may not be welded or otherwise secured to the screw), the disclosed implant may selectively provide for motion and/or limited motion and/or fusion between the implant components, depending upon the amount of compression placed on the screw and sleeve construct by the collet or nut (and/or any relevant surface texturing that may be incorporated into the various disclosed articulating surfaces).

As previously noted, the assembled implant can desirably include one or more articulating surfaces. For example, the implant can incorporate sliding/articulating surfaces 360 and 570 proximate a midpoint of the screw body which can allows the threaded axis cage to articulate relative to the screw body—essentially creating a ball joint allowing for motion preservation of the SI joint (0-20 degrees). In addition, a concavity or reduced diameter surface 312 can be positioned at a location proximal to the ball joint articulation, which can allow additional articulation between the threaded axis cage and screw body, as well as improve structural integrity and/or reduce stress risers in the implant.

In a similar manner, relative motion between the smooth, flattened surface 450 of the nut and the inner shoulder 595 of the sleeve can allow some sliding therebetween, which further facilitate such motion. When the threaded axis cage and the screw body are secured in their respective positions by the nut, the articulating surface(s) desirably allows the attached sacrum and the iliac crest bone structures (See FIG. 8D) to move relative to each other (e.g., about the central screw axis), while maintaining a desired spacing between the attached bones (See FIGS. 8A through 8C). The head of the axis cage may have an articulating surface to allow for the collet to attach and retain the screw.

In various embodiments, the middle region (e.g., unthreaded region) of the screw body and cage can incorporate a relatively wider region or fissure. Desirably, the fissure region can be positioned across a treated SI joint, with the modularity and/or sizing of the cage and screw components allowing a physician to select and place the implant to accommodate any anatomical size, deformity or age of patient in a desired manner.

The various components of the implant can be formed by machining, molding and/or other known manufacturing techniques, from a durable material usable in the prosthetic arts that is desirably not subject to significant bio-absorption or resorption by surrounding bone or tissue over time. The implant structure is intended to remain in place to stabilize the treatment site. Such materials include, but are not limited to, titanium, titanium alloys, tantalum, titanium (aluminum, vanadium, and titanium), chrome cobalt, surgical steel, or any other total joint replacement metal and/or ceramic, sintered glass, artificial bone, any uncemented metal or ceramic surface, or various combinations thereof. Various high strength plastics and/or other known orthopedic materials may similar be incorporated herein.

In the embodiments described herein, a variety of manufacturing steps and/or processes may be performed to create a desired implant and/or component(s) thereof, including the use of different manufacturing processes to create a single implant and/or the employment of multiple different manufacturing processes to create components that may be ultimately assembled into a single implant. Such processes could include casting, molding (including injection molding), subtractive machining (i.e., milling and drilling), additive machining (i.e., additive 3D printing), and/or other manufacturing methods know in the art. If desired, implants could be constructed from a variety of modular components, including modular components comprising different materials. If desired, such modular components could be provided in a kit form for selection and/or assembly in a surgical theatre and/or in situ during a surgical procedure. If desired, various components may be removable and replaceable in a single assembly.

If desired, one or more bony in-growth or through-growth regions may extend along portions and/or the entire outer and/or inner surface(s) of the implant structure, and/or bony in-growth or through-growth region may cover specified regions of the implant. The bony in-growth region(s) or through-growth can comprise, e.g., through holes, and/or various surface patterns, and/or various surface textures, and/or pores, or combinations thereof. The configuration of the bony in-growth or through-growth region(s) can, of course, vary. By way of examples, the bony in-growth or through-growth region can comprise holes or fenestrations, or an open mesh configuration, or beaded configuration, or a trabecular configuration; or any combinations thereof. In one preferred embodiment, a bony in-growth region or through-growth region may comprise a porous plasma spray coating on the implant or components thereof. This creates a biomechanically rigorous fixation/fusion system, designed to support reliable fixation/fusion and acute weight bearing capacity. The bony in-growth or through-growth region(s) may further be covered with various other coatings such as antimicrobial, antithrombotic, and osteoinductive agents, or a combination thereof.

FIG. 6A depicts a perspective view of one exemplary embodiment of an insertion tool 600 for use with an assembled implant. FIG. 6B depicts a perspective view of the insertion tool 600 with an attached implant at a distal end thereof, with FIG. 6C depicting a partial end view of the insertion tool and attached implant. FIG. 6D depicts an exploded view of the insertion tool 600.

As best seen in FIG. 6D, the insertion tool 600 includes an outer tube 605 with a hollow lumen, a collet shaft 610, a collet inserter 615, a driver shaft body 620, an inner knob 625, an outer handle 630, an outer knob 635 and attachment pins 640 of varying shapes and/or sizes. The driver shaft body 620 includes a driver head 622 at a distal end thereof which engages with and articulates into the screw body, and an inner knob 625 which is secured to the driver shaft body 620 via an attachment pin 640 and shaft groove 627 (such that the inner knob 625 freely rotates about the driver shaft body 620). A proximal end of the driver shaft body 620 incorporates a ¼ inch square taper attachment 629.

The collet inserter 615 includes an internally threaded proximal end 616 which engages with an externally threaded distal end 611 of the collet shaft 610. A distal end of the collet inserter 615 includes a plurality of curved or angled grasping fingers 617 which, when the collet inserter 615 is drawn into the outer tube 605, cause the grasping fingers 617 to compress, grasping and retaining a threaded axis cage (see FIGS. 6C and 8F). The threaded axis cage can be grasped or released with the control of the collet adjuster handle through counter or counterclockwise rotation. As best seen in FIG. 7B, the fingers can incorporate and angle of B degrees, such as 5, 10 and/or 15 degrees, or others, if desired.

The driver shaft body 620 is desirably slightly longer than the length of the collet shaft 610 and inserter 615, such that the driver head can extend through the lumens of the collet shaft 610 and inserter 615 and desirably engage with a corresponding proximal tip of the screw body (See FIG. 8E). The ¼ inch square taper attachment of the driver shaft body 620 desirably allows connection of a surgical t-handle to desirably control the implant driver and collet handle in unison. The implant driver can include an engagement feature 628 which engages with a corresponding shaped interior lumen of the collet shaft 610, desirably rotationally interlocking the implant driver and collet shaft together and allowing them to be rotated in unison such that the implant can be inserted as a unit (e.g., in a single action). If desired, the driver head and corresponding proximal tip of the screw body can comprise a wide variety of screw drive and socket engagement features, including, but not limited to, slotted, cruciform, square, multiple square, internal hex, pentalobular, hexalobular (e.g., Torx), combination and/or many other known screw drive and socket combinations.

FIG. 6E depicts one alternative embodiment of a trim driver shaft body having a rounded and/or smooth outer shaft section 680 (e.g., replacing the engagement feature 628 of the driver shaft body 620), which allows the trim driver shaft body to rotate and/or spin separately from the collet shaft 610. In this embodiment, the outer diameter (OD) of the trim driver shaft body 620 can desirably be slightly smaller than the inner diameter (ID) of the collet shaft 610 and inserter 615, with the trim driver shaft body capable of freely spinning inside the collet shaft without rotating the threaded axis cage 500. This arrangement desirably allows for independent rotational operation of the screw body from the cage, such as for implantation and/or extraction of the screw body portion of the implant only and/or independent adjustment of the screw body and cage. Desirably, the handle/knob of the trim driver tool can incorporate a different shape, color and/or texture from the driver shaft body, for ease of user recognition and utilization.

In use, the trim driver can be utilized to rotate and/or adjust the placement and depth of the screw body independently of the collet shaft and attached threaded axis cage. If desired, independent rotation of the screw body and the threaded axis cage can alter placement of each component to a desired position, as well as provide for a desired amount of stabilization, including compression and/or distraction, if any, across the SI joint. Moreover, fracture fixation can be easily addressed by the various components of the disclosed system and methods. Even for fractures with Denis classification zones 1, 2 and 3, the proper selection and placement of the screw body and associated threaded axis cage allows the surgeon to use the cage and the screw independently to trim and/or adjust fracture fragments into a desired orientation and/or position relative to other anatomy (e.g., anatomic restoration)

FIGS. 7A and 7B depict views of a collet inserter 700. The collet inserter 700 desirably grasps and articulates the cage of the implant at the very end of the insertion tool, using from 3 to 8 collet fingers 710. In use, the collet inserter 700 can be utilized to control implant insertion and/or positioning, as well as retain the implant within the insertion tool until such time as the implant is deployed. Functionally, the grasping action of the fingers are controlled by rotation of the collet shaft 610. By rotating the collet shaft 610 clockwise, the collet inserter is drawn into the outer tube, which compresses the collet fingers around the implant and thereby tightening the collet fingers around the implant articulations. Conversely, counterclockwise rotation of the collet shaft 610 causes the collet inserter to be pushed out of the outer tube, allowing the fingers to decompress and release the implant.

FIGS. 9A and 9B are, respectively, anterior and posterior anatomic views of the human hip girdle comprising the sacrum and the hip bones (the right ilium, and the left ilium), the sacrum being connected with both hip bones at the sacroiliac joint (e.g., the SI-Joint);

Imaging and/or Anatomical Modeling

It should be understood that the various procedures described herein can be accomplished using a variety of direct and/or indirect imaging and/or visualization techniques, by employing surgical navigation and/or haptic controls, and/or using anatomical models using autonomous surgical devices such as surgical robots. A wide variety of imaging and/or visualization techniques are contemplated herein, including but not limited to x-ray, cone beam CT, C- and O-Arm systems, digital tomosynthesis, ultrasound, laser imaging, MRI, CT, PET, SPECT, and/or other images and combinations thereof. In other embodiments, it may be desirable to model various patient measurements and/or imaging information to simulate the targeted bones/joint(s) and/or surrounding anatomy virtually. Such simulations can include virtually modeling the alignment and/or load bearing conditions of various bones, joints and/or surrounding anatomical structures. Such simulations can be used to obtain valuable anatomical, biomechanical and/or kinematic data including the loaded condition of various joint components, component positions, component movement, joint and/or surrounding tissue anatomical or biomechanical constraints or limitations, as well as estimated mechanical axes in one or more directions (i.e., coronal, sagittal or combinations thereof). In addition to creating a patient-specific anatomic model, this information could also be utilized (alone or in combination with other data described herein) to design and/or select various features of the implants, devices, surgical procedures and/or tools described herein.

In the various embodiments described herein, one or more steps of an imaging, assessment, selection, and/or implant design may be partially or fully automated, for example, using a computer-run software program and/or one or more robotic surgical tools. In various embodiments, processing of patient data, the assessment of biological features and/or feature measurements, the assessment of implant component features and/or feature measurements, the optional assessment of surgical approaches and/or the selection and/or design of one or more features of the implant component(s), and/or the implantation procedure(s) itself, may be partially or wholly automated. For example, patient data, with optional user-defined parameters, may be inputted or transferred by a user and/or by electronic transfer into a software-directed computer system that can identify variable implant component features and/or feature measurements and perform operations to generate one or more virtual models and/or implant specifications, for example, in accordance with one or more target or threshold parameters. Implant selection and/or design data, with optional user-defined parameters, may be inputted or transferred by a user and/or by electronic transfer into a software-directed computer system that performs a series of operations to transform the data and optional parameters into one or more implant recommendations and/or specifications. Selected implant data, optionally with user-defined parameters, may be inputted or transferred by a user and/or by electronic transfer into a software-directed computer system that performs a series of operations to transform the data and optional parameters into one or more surgical procedure specifications or instructions. Implant data, or surgical procedure data, optionally with user-defined parameters, may be inputted or transferred by a user and/or by electronic transfer into a software-directed computer system that directs one or more automated and/or semi-automated surgical instruments, for example, a robot, to perform one or more surgical steps. In certain embodiments, one or more of these actions can be performed as steps in a single process by one or more software-directed computer systems. Similarly, such modeling and/or anatomic information could be used to provide a surgeon performing the surgical implantation procedure with surgical navigation data generated using a surgical navigation system (which can include image guided as well as non-image guided systems).

Procedure for Arthroplasty

Initially, a physician can identify the bone regions that are to be treated. As one example, the physician may be aided by conventional visualization techniques, e.g., using X-ray image intensifiers such as C-arms or fluoroscopes to produce a live image feed which is displayed on a monitor, TV screen or other display such as an optical head mounted display (e.g., Google Glasses), wherein a guide pin can be introduced by conventional means through the one adjacent bone region, through the intervening space or joint, and partially into the other adjacent bone region. For treating a SI-joint under X-ray or other direct visualization, a K-wire can be inserted in the first sacral body, desirably avoiding important structures by staying within the cortex of the bone. The length for the screw can be determined by the measurements inscribed on the K-wire, or using known imaging modalities and techniques. After the K-wire is in the desired placement using a lateral or lateral oblique approach, per surgeon preference, the hole can optionally be pre-drilled for the desired screw length using a cannulated drill bit. The K-wire will desirably stay in place as a guide until the implant is inserted. The selected implant is attached to the inserter and retained to the inserter by the collet which is tightened to the implant by the collet adjuster. Once the collet is tightened, the implant and the implant driver are inserted into the lumen of the collet drive and is fixed to the collet drive by clockwise tightening of the collet attachment handle. A t-handle is attached to the ¼ square attachment point of the implant driver. The implant is threaded onto the k-wire and inserted into the pre-drilled hole by ways of clockwise rotation of the t-handle. The implant is screwed into the joint by ways of clockwise rotation of the t-handle. The implant may be inserted via a lateral approach (See FIGS. 10A through 10C) and/or the implant may be inserted via a postero-lateral approach (See FIGS. 11A through 11C), as well as using other surgical approaches known to those of skill in the art.

Once the implant has been fully inserted and tightened into the iliac bone through the SI joint and into the sacrum, the implant driver can be removed from the collet. This is done with counterclockwise rotation of the collet attachment handle. Next the trim driver is inserted into the collet handle and fastened in the identical fashion as the implant drive.

The T-handle is attached and the surgeon can rotate approximately ¾ of a turn to stabilize the joint space in a desired manner, which may include compression, distraction and/or other stabilization of the joint's bony components, at the surgeon's option. The collet handle is then detached after removal of the trim adjuster by counterclockwise rotation of the collet adjuster to release the collet.

Procedure for Fusion

There can be many instances where a physician wishes to limit and/or prevent motion using the disclosed system and components. As one example, under X-ray or using other visualization methods, the surgeon has the option to insert a K-wire in the first sacral body avoiding important structures by staying within the cortex of the bone. The length for the screw is determined by the measurements inscribed on the K-wire or imaging. After the K-wire is in the desired placement using a lateral or lateral oblique approach, per surgeon preference, the hole is pre-drilled for the desired screw length using a cannulated drill bit. The K-wire stays in place as a guide until the implant is inserted. The selected implant is attached to the inserter and retained to the inserter by the collet which is tightened to the implant by the collet adjuster. Once the collet is tightened, the implant and the implant driver are inserted into the lumen of the collet drive and is fixed to the collet drive by clockwise tightening of the collet attachment handle. A t-handle is attached to the ¼ square attachment point of the implant driver. The implant is threaded onto the k-wire and inserted into the pre-drilled hole by ways of clockwise rotation of the t-handle. The implant is screwed into the joint by ways of clockwise rotation of the t-handle.

Once the implant has been fully inserted and tightened into the iliac bond through the SI joint and into the sacrum, the implant driver is removed from the collet. This is done with counterclockwise rotation of the collet attachment handle. Next the trim driver is inserted into the collet handle and fastened in the identical fashion as the implant drive. The T-handle is attached and surgeon adds any final tightening to create SI joint compression/stabilization and/or fixation with a clockwise rotation of the T-handle.

A second and third implant can be inserted anywhere in the sacral body using the same process as the first implant, only that they are inserted in a different location of the sacrum (see FIGS. 12A and 12B).

Procedure for Fusion after Arthroplasty

Assuming two implants are already present in the S1 and S2 bodies on the ipsilateral side, the surgeon has an option of performing a second surgical procedure at a later date to fuse the joint instead of utilizing the arthroplasty with a lateral or lateral oblique approach.

First, the two or more implants in the body are identified, and the scar tissue is debrided to expose the heads of the implants. The collet is opened with counterclockwise rotation of the collet adjuster. The collet driver is then fixed over the head implant and articulating with the collet channels. The collet prongs are tightened to the implant with clockwise rotation of the collet adjuster. The collet is checked for snug contact with the implant. The trim adjuster is then placed into the lumen of the collet and fastened to the collet using clockwise rotation of the collet attachment handle. The screw portion of the implant is tightened to feel creating compression of the SI joint space. Next the trim adjuster and the collet are removed from the implant with counterclockwise rotation of the collet adjuster. This process is repeated for the second implant.

Next, a 3rd implant is placed into the body. Under imaging, the surgeon has the option to insert a K-wire in the 3rd sacral body avoiding important structures by staying within the cortex of the bone. The length for the screw is determined off of the K-wire markings. After the K-wire is in the desired placement per surgeon preference, the hole is pre-drilled for the desired screw length using a cannulated drill bit. The K-wire stays in place as a guide until the implant is inserted. The selected implant is attached to the inserter and retained to the inserter by the collet which is tightened to the implant by the collet adjuster. Once the collet is tightened to the implant, the implant driver is inserted into the lumen of the collet driver. The driver is fixed to the collet driver by clockwise tightening of the collet attachment handle. A t-handle is attached to the ¼ square attachment point of the implant driver. The implant is threaded onto the k wire and inserted into the pre-drilled hole by ways of clockwise rotation of the t-handle. The implant is screwed into the joint using clockwise rotation of the T-handle.

Once the implant has been fully inserted and tightened into the iliac bond through the SI joint and into the sacrum the implant driver is removed from the collet. This is done with counterclockwise rotation of the collet attachment handle. Next the trim driver is inserted into the collet handle and fastened in the identical fashion as the implant drive was. The T-handle is attached and surgeon adds any final tightening creating SI joint compression, stabilization and fixation with a clockwise rotation of the T-handle.

A wide variety of potential clinical uses incorporating the disclosed devices can be contemplated, including, but not limited to: (1) joint arthroplasty using a technique of 1 or more implants and joint distraction with stabilization, (2) joint arthroplasty using a technique of 2 or more implants, inline and joint distraction with stabilization, (3) revision of arthroplasty using compression of 1 or more implants inserted in a curvilinear approach, (4) joint fusion with 3 or more implants inserted in a curvilinear approach using distraction, (5) joint fusion with 1 or more implants inserted in a curvilinear approach using compression and stabilization, (6) temporary joint arthroplasty using a technique of 1 or more implants and joint distraction followed by implant excision in a second procedure, (7) temporary joint arthroplasty using a technique of 3 or more implants, inline and joint distraction and stabilization, (8) temporary joint fusion with 1 or more implants inserted in a curvilinear approach using distraction and stabilization followed by implant excision in a second procedure, (9) fusion or arthroplasty can be obtained with 1 or more screws protruding through the iliac bone and anchoring to any part of the sacral interbody or adjacent, and/or (10) various combinations and/or portions of combinations thereof.

The implant assemblies, tools and techniques described herein make possible surgical techniques that are less invasive than traditional open surgery with no extensive soft tissue stripping. The lateral or lateral oblique approaches to the SI-Joint provide straightforward surgical approaches that complement the minimally invasive surgical techniques. The profile and design of the implant assemblies minimize rotation and/or micromotion, and the stabilization provided by the titanium or other rigid materials desirably provide immediate post-op SI Joint stability. The bony in-growth region(s) can support stable bone fixation/fusion. The implant assemblies and related surgical approaches make possible the treatment of multiple joint locations designed to optimize post-surgical weight bearing capacity and provide a biomechanically rigorous implant designed specifically to stabilize the heavily loaded SI-Joint.

Using either a lateral or a lateral oblique approach, one or more implant assemblies can be individually inserted in a minimally invasive fashion across the SI-Joint, as has been described herein. Conventional tissue access tools, obturators, cannulas, and/or drills can be used for this purpose. No joint preparation, removal of cartilage, or scraping would be required before formation of the insertion path or insertion of the implant assembly, so a minimally invasive insertion path sized approximately at or about the maximum outer diameter of the implant assemblies need be formed.

If desired, an insert could be constructed from a variety of modular components, including modular components comprising different materials. If desired, such modular components could be provided in a kit form for selection and/or assembly in a surgical theatre and/or in situ during a surgical procedure. If desired, various components may be removable and replaceable.

Various surgical methods for preparing anatomical surfaces and/or for implanting or placement of the various devices and/or components described herein are also described, including the insertion and placement of implants between adjacent bones and/or bone structures or other body locations.

While embodiments and applications of the present subject matter have been shown and described, it would be apparent that other embodiments, applications and aspects are possible and are thus contemplated and are within the scope of this application. The subject matter, therefore, is not to be restricted except in the spirit of the appended claims.

All references, including publications, patent applications, and patents, cited herein are hereby incorporated by reference to the same extent as if each reference were individually and specifically indicated to be incorporated by reference and were set forth in its entirety herein.

The various headings and titles used herein are for the convenience of the reader and should not be construed to limit or constrain any of the features or disclosures there-under to a specific embodiment or embodiments. It should be understood that various exemplary embodiments could incorporate numerous combinations of the various advantages and/or features described, all manner of combinations of which are contemplated and expressly incorporated hereunder.

As previously noted, the use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., i.e., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An implant for sacroiliac joint arthroplasty, comprising:
a bone screw having a shank with a proximal end and a distal end, the shank defining a longitudinal axis from the proximal end to the distal end with an internal bore extending along the longitudinal axis from the proximal end to the distal end, the proximal end having a sleeve engagement portion comprising a proximally facing first articulating surface and a central shaft having an externally facing threaded portion;
a cylindrical sleeve having a distally facing second articulating surface and a central bore with a proximal shoulder positioned therein, the central bore being larger than the central shaft to allow the cylindrical sleeve to tilt relative to the bone screw as the proximally facing first articulating surface articulates with the distally facing second articulating surface; and
a securement component which selectively engages with the externally facing threaded portion to secure the cylindrical sleeve into engagement with the bone screw while permitting articulation between the proximally facing first articulating surface and the distally facing second articulating surface, wherein the securement component can be selectively tightened from a first position which allows relative motion between the bone screw and the sleeve to a second position which inhibits relative motion between the bone screw and the sleeve.

2. The implant of claim 1, wherein the bone screw includes an externally threaded shank portion proximate to the distal end of the shank, and the cylindrical sleeve includes an externally threaded sleeve portion.

3. The implant of claim 2, wherein a shank thread of the externally threaded shank portion is in a same direction as a sleeve thread of the externally threaded sleeve portion.

4. The implant of claim 2, wherein a shank thread of the externally threaded shank portion is in an opposing direction of a sleeve thread of the externally threaded sleeve portion.

5. The implant of claim 1, wherein the proximal end of the shank includes a first driving section for engagement with a first driving tool.

6. The implant of claim 5, wherein a proximal end of the cylindrical sleeve includes a plurality of notches or detents for engagement with a second driving tool.

7. The implant of claim 6, wherein the shank can be rotated by the first driving tool independent of rotation of the cylindrical sleeve by the second driving tool.

8. The implant of claim 1, wherein when the cylindrical sleeve is positioned over the shank, the externally facing threaded portion is fully contained within the central bore of the cylindrical sleeve.

9. A method for the arthroplasty of the sacroiliac joint, comprising:
creating an insertion path through the ilium, across the sacroiliac joint, and into the sacrum;
inserting an implant having a longitudinal axis through the insertion path into the ilium, through the sacroiliac joint, and into the sacrum, the implant comprising:
a generally cylindrical elongated body having a first external screw thread extending proximately from a distal end thereof, a second external thread extending proximately from a proximal end thereof, a non-threaded section extending between the first and second external screw threaded portions and a proximally facing engagement surface,
a generally cylindrical sleeve having a third external screw thread, the generally cylindrical sleeve sized and configured to pass over the second external thread and the non-threaded section of the generally cylindrical elongated body, the generally cylindrical sleeve including a distally facing second engagement surface, the distally facing second engagement surface configured to contact the proximally facing engagement surface of the generally cylindrical elongated body when the generally cylindrical sleeve is positioned over the generally cylindrical elongated body, and
a collet or nut having an internally threaded bore, the collet or nut being sized and configured to engage with the second external thread, whereby tightening or loosening of the collet or nut on the second external thread selectively alters a contact force between the distally facing second engagement surface and the proximally facing engagement surface,
anchoring the first external screw thread of the generally cylindrical elongated body in an interior region of the sacrum;
anchoring the third external screw thread of the generally cylindrical sleeve into an interior region of the ilium; and positioning at least a portion of the proximally facing engagement surface and at least a portion of the distally facing second engagement surface within the sacroiliac joint.

10. The method of claim 9, further comprising adjusting the collet or nut onto the second external thread to secure the distally facing second engagement surface into intimate contact with the proximally facing engagement surface.

11. The method of claim 10, further comprising adjusting the collet or nut onto the second external thread to prevent relative motion between the distally facing second engagement surface and the proximally facing engagement surface.

12. The method of claim 9, further comprising adjusting the collet or nut onto the second external thread to allow the distally facing second engagement surface to become spaced apart from the proximally facing engagement surface.

13. The method of claim 9, wherein the step of inserting the implant having a longitudinal axis through the insertion path into the ilium, through the sacroiliac joint, and into the sacrum is accomplished via a lateral approach.

14. The method of claim 9, wherein the step of inserting the implant having a longitudinal axis through the insertion path into the ilium, through the sacroiliac joint, and into the sacrum is accomplished via a postero-lateral approach.

15. The method of claim 9, wherein the steps of anchoring the first external screw thread of the generally cylindrical elongated body in an interior region of the sacrum and anchoring the third external screw thread of the generally cylindrical sleeve into an interior region of the ilium result in compression of the sacrum towards the ilium.

16. The method of claim 9, wherein the steps of anchoring the first external screw thread of the generally cylindrical elongated body in an interior region of the sacrum and anchoring the third external screw thread of the generally cylindrical sleeve into an interior region of the ilium result in distraction of the sacrum away from the ilium.

17. The method of claim 9, wherein the steps of anchoring the first external screw thread of the generally cylindrical elongated body in an interior region of the sacrum and anchoring the third external screw thread of the generally cylindrical sleeve into an interior region of the ilium induce the sacrum to fuse to the ilium.

18. The method of claim 9, wherein the steps of anchoring the first external screw thread of the generally cylindrical elongated body in an interior region of the sacrum and anchoring the third external screw thread of the generally cylindrical sleeve into an interior region of the ilium allow relative motion between the sacrum and the ilium.

19. The method of claim 9, wherein the generally cylindrical sleeve can be rotated relative to the generally cylindrical elongated body when the collet or nut is positioned on the second external thread in a loosened configuration.

20. The method of claim 9, wherein the generally cylindrical sleeve is inhibited or prevented from rotating relative to the generally cylindrical elongated body when the collet or nut is positioned on the second external thread in a tightened configuration.

\* \* \* \* \*